United States Patent
Eugenin et al.

(10) Patent No.: US 9,540,646 B2
(45) Date of Patent: Jan. 10, 2017

(54) CELLULAR TARGETS FOR HIV INFECTION

(71) Applicant: ALBERT EINSTEIN COLLEGE OF MEDICINE OF YESHIVA UNIVERSITY, Bronx, NY (US)

(72) Inventors: Eliseo Eugenin, Eastchester, NY (US); Joan W. Berman, New York, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 36 days.

(21) Appl. No.: 14/381,727

(22) PCT Filed: Feb. 28, 2013

(86) PCT No.: PCT/US2013/028160
§ 371 (c)(1),
(2) Date: Aug. 28, 2014

(87) PCT Pub. No.: WO2013/134030
PCT Pub. Date: Sep. 12, 2013

(65) Prior Publication Data
US 2015/0057331 A1 Feb. 26, 2015

Related U.S. Application Data

(60) Provisional application No. 61/606,696, filed on Mar. 5, 2012.

(51) Int. Cl.
| | |
|---|---|
| C12N 15/11 | (2006.01) |
| C12N 15/113 | (2010.01) |
| A61K 38/08 | (2006.01) |
| A61K 45/06 | (2006.01) |
| A61K 31/00 | (2006.01) |
| A61K 31/7076 | (2006.01) |
| A61K 31/17 | (2006.01) |
| A61K 31/427 | (2006.01) |
| A61K 31/4439 | (2006.01) |
| A61K 31/661 | (2006.01) |
| A61K 31/713 | (2006.01) |

(52) U.S. Cl.
CPC ........... *C12N 15/1132* (2013.01); *A61K 31/00* (2013.01); *A61K 31/17* (2013.01); *A61K 31/427* (2013.01); *A61K 31/4439* (2013.01); *A61K 31/661* (2013.01); *A61K 31/7076* (2013.01); *A61K 31/713* (2013.01); *A61K 38/08* (2013.01); *A61K 45/06* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 2003/0087247 A1 | 5/2003 | Kumamoto et al. | |
| 2003/0087273 A1* | 5/2003 | Holzmayer | G01N 33/56988 435/6.16 |

FOREIGN PATENT DOCUMENTS

WO 2012019991 A1 2/2012

OTHER PUBLICATIONS

Hazleton et al, ATP Signaling is Critical for HIV Entry into Primary Human Macrophages, Oct. 2010, Journal of Neurovirology, vol. 16, No. Suppl. 1, pp. 36-37.*
Rettinger et al, Profiling at recombinant homomeric and heteromeric rat P2X receptors identifies the suramin analogue NF449 as a highly potent P2X1 receptor antagonist, 2005, Neuropharmacology, 48: 461-468.*
PCT International Search Report and Written Opinion, dated Jun. 3, 2013 in connection with PCT International Application No. PCT/US2013/28160, 14 pages.
Hazleton J E et al., entitled "Purinergic receptors are required for HIV-1 infection of primary human macrophages," ProQuest Dissertation and Theses, pp. 1-261, 2011. Article retrieved from the ProQuest Dissertations & Theses Full Text: The Sciences and Engineering Collection.
Seror C et al., entitled "Extracellular ATP acts on P2Y2 purinergic receptors to facilitate HIV-1 infection," J. Exp. Med. vol. 208, No. 9, pp. 1823-1834, Aug. 22, 2011.
Swartz T H et al., entitled "HIV-1 Cell-Cell Infection is Inhibited by Purinergic Receptor Antagonists by Blocking Viral Membrane Fusion within Virological Synapse Target Cells," Mar. 2013. Article retrieved from the internet, URL: <http://www.retroconference.org/2013b/PDFs/194.pdf>.
Hazleton J E et al., entitled "Purinergic receptors are required for HIV-1 infection of primary human macrophages," J Immuol, vol. 188, pp. 4488-4495, Mar. 26, 2012.

* cited by examiner

*Primary Examiner* — Kate Poliakova-Georgantas
(74) *Attorney, Agent, or Firm* — Amster, Rothstein & Ebenstein LLP

(57) ABSTRACT

Methods and compositions are provided for treating HIV infection and for inhibiting HIV infection, and for identifying purinergic receptor antagonists or Panx 1 hemi-channel blockers useful therefor. The invention provides a method of treating a mammalian subject having an HIV infection, or suspected of having been exposed to HIV, comprising administering to the mammalian subject an amount of (i) an antagonist of a Panx 1 hemichannel, or (ii) of an inhibitor of a purinergic receptor, effective to inhibit (a) HIV fusion with a target cell, or (b) HIV replication, or (c) HIV entry into a target cell, or two or more of (a), (b) and (c).

4 Claims, 11 Drawing Sheets

CELLULAR TARGETS FOR HIV INFECTION

CROSS-REFERENCE TO RELATED APPLICATIONS

This application is a U.S. national stage entry under 35 U.S.C. §371 of PCT International Patent Application No. PCT/US2013/28160, filed Feb. 28, 2013, which claims benefit of U.S. Provisional Application No. 61/606,696, filed Mar. 5, 2012, the contents of each of which are incorporated herein by reference into the subject application.

STATEMENT OF GOVERNMENT SUPPORT

This invention was made with government support under grant numbers MH070297, MH075679, MH083497, DA025567 and MH076679 awarded by the National Institute of Mental Health and grant number AI-051519 from the National Institutes of Health. The government has certain rights in the invention.

BACKGROUND OF THE INVENTION

Throughout this application various publications are referred to by number in parenthesis. Full citations for these references may be found at the end of the specification immediately preceding the claims. The disclosures of these publications are hereby incorporated by reference in their entireties into the subject application to more fully describe the art to which the subject application pertains.

Human immunodeficiency virus-1 (HIV) infects mostly immune cells by binding of the viral envelope protein gp120 to the host cellular proteins, CD4 and CCR5 and/or CXCR4, resulting in fusion of the viral envelope with the cellular membrane. To date, in addition to CD4, CCR5 and/or CXCR4, no other membrane cellular proteins have been identified to participate directly in the process of viral entry (1). However, a few studies indicated that upon binding of the virus to its cellular receptors, intracellular $Ca^{2+}$ levels rise (2-4) and opening of non-selective cation channels as well as calcium activated $K^+$ channels occurs (5), suggesting that signaling and activation of other proteins may be required for infection and replication. Recently, studies in cell lines and peripheral blood mononuclear cells (PBMCs) indicated that ATP release through pannexin1 (Panx1) hemichannels is required for FEW replication (6), supporting the hypothesis that additional host proteins are required for infection/replication.

Hemichannels are plasma membrane channels that can be open at the unapposed cell surface, forming aqueous conduits permeable to ions and small molecules (e.g., ATP, glutamate, NAD+, and PGE2). They allow diffusional exchange between the intra- and extracellular compartments, constituting a route for autocrine/paracrine cellular communication (7). Hemichannels are constituted by the oligomerization of six protein subunits termed connexins (Cxs) or pannexins (Panxs), both highly conserved protein families encoded by 21 or 3 genes in humans, respectively (8, 9). Panx1 hemichannels in concert with purinergic receptors have been described to be important in different immune functions, including cellular activation (10-12), apoptosis (13), stress signals (14), secretion of inflammatory cytokines (15) and HIV replication (6). However, how HIV infection changes the opening of these channels in primary human CD4+ T lymphocytes, one of the main targets of HIV, remains to be elucidated.

Additionally, it is known that macrophages are critical for HIV infection and spread within the host. They are the first cells to become infected and serve as a viral reservoir (45-49). Macrophage infection does not result in cell death and HIV infected macrophages can persist for long periods of time in host tissues even in the presence of combined antiretroviral therapy (50-53). Infected macrophages in the CNS are also important mediators of HIV-associated neurocognitive disorders, secreting inflammatory mediators and neurotoxic proteins that result in CNS dysfunction (54, 55).

HIV infects macrophages by binding of the envelope protein gp120 to CD4 and then CCR5 receptors and subsequent fusion with the host cell membrane (56-58). Binding of gp120 results in increased intracellular calcium and G-protein signaling (59-61) that involve opening of non-selective cation channels and calcium activated potassium channels (62). However, additional specific host proteins that participate in this process need further evaluation.

Purinergic receptors are activated by extracellular ATP and its byproducts, including ADP and UTP, and are classified intro three groups: adenosine receptors (P1), ATP-gated cation channels (P2X), and G-protein coupled receptors (P2Y). Activation of P2X or P2Y receptors causes an increase in intracellular calcium (19). This laboratory's and other results indicate that macrophages predominantly express $P2X_1$, $P2X_4$, $P2X_7$, $P2Y_1$, $P2Y_2$, $P2Y_4$, $P2Y_6$, and $P2Y_{12}$ receptors (64, 65). P2X and P2Y receptors in macrophages are important mediators of the response to host injury, recognizing extracellular ATP as a damage signal that induces inflammation through cytokine release and superoxide formation (66-68). Additionally, recent studies showed that ATP release and purinergic receptor signaling are activated in response to infectious agents (69, 70).

The present invention addresses the need for novel treatments for HIV infection and inhibition of HIV infection and assays for identifying agents therefor.

SUMMARY OF THE INVENTION

The invention provides a method of treating a mammalian subject having an HIV infection, or suspected of having been exposed to HIV, comprising administering to the mammalian subject an amount of (i) an antagonist of a Panx1 hemichannel, or (ii) of an inhibitor of a purinergic receptor, effective to inhibit (a) HIV fusion with a target cell, or (b) HIV replication, or (c) HIV entry into a target cell, or two or more of (a), (b) and (c).

Also provided is an assay method for identifying a purinergic receptor inhibitor or Panx1 antagonist as a candidate treatment for an REV infection, comprising experimentally determining HIV replication in an HIV-infected cell under conditions permissive of HIV replication and contacting the REV-infected cell with the purinergic receptor inhibitor or Panx1 antagonist and experimentally determining HIV replication in the cell under the conditions permissive of HIV replication in the presence thereof, and identifying the purinergic receptor inhibitor or Panx1 antagonist as a candidate treatment for an HIV infection, wherein a reduction in, or inhibition of, HIV replication in the HIV-infected cell in the presence of the purinergic receptor inhibitor or Panx1 antagonist as compared to HIV replication in the HIV-infected cell in the absence of the purinergic receptor inhibitor or Panx1 antagonist, respectively, indicates that the purinergic receptor inhibitor or Panx1 antagonist is a candidate treatment for HIV infection.

Also provided is an assay method for identifying a purinergic receptor inhibitor or Panx1 antagonist as a candidate treatment for preventing or inhibiting HIV infection in a mammalian subject or reducing the likelihood of HIV infection, comprising experimentally determining HIV entry into, or fusion with, a target cell, under conditions permissive of HIV entry into, or fusion with, a target cell and contacting the HIV-infected cell with the purinergic receptor inhibitor or Panx1 antagonist and experimentally determining HIV entry into, or fusion with, a target cell under the conditions permissive of HIV entry into, or fusion with, the target cell in the presence thereof, and identifying the purinergic receptor inhibitor or Panx1 antagonist as a candidate treatment for preventing or inhibiting HIV infection in a mammalian subject or reducing the likelihood of HIV infection, wherein a reduction in, or inhibition of HIV replication in the HIV-infected cell in the presence of the purinergic receptor inhibitor or Panx1 antagonist as compared to in the absence of the purinergic receptor inhibitor or Panx1 antagonist, respectively, indicates that the purinergic receptor inhibitor or Panx1 antagonist is a candidate treatment for preventing or inhibiting HIV infection or reducing the likelihood of HIV infection.

Also provided is a purinergic $P2X_1$, $P2X_7$ and $P2I_1$ receptor inhibitor for treatment of an HIV infection or for inhibition or prevention of an HIV infection.

Also provided is a Panx1 hemichannel antagonist for treatment of an HIV infection or for inhibition or prevention of an HIV infection.

DETAILED DESCRIPTION OF THE INVENTION

Figures 1A, 1B, 1C, 1D, 1E, 1F:
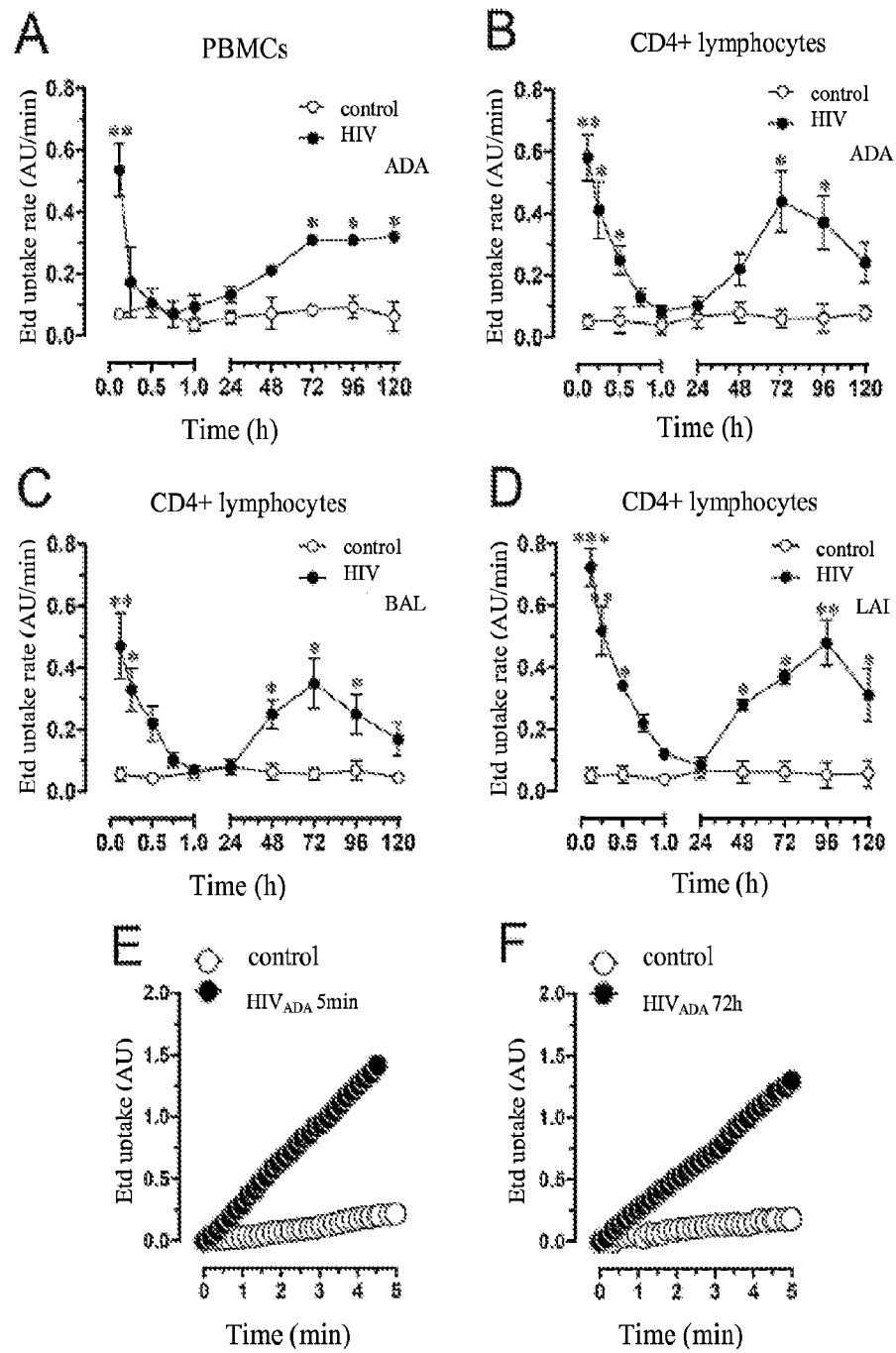
FIG. 1A-1F. HIV increases Etd uptake in a biphasic manner in human primary PBMCs and $CD4^+$ T lymphocytes. (AD) Time course of Etd uptake rate obtained from PBMCs or $CD4^+$ T lymphocytes under control conditions (white circles) or after infection with HIV (black circles), 0 to 120 h. PBMCs infected with $HIV_{ADA}$ (A); $CD4^+$ T lymphocytes infected with $HIV_{ADA}$ (B), $HIV_{Bal}$ (C) or $HIV_{LAI}$ (D). (E, F) Representative time lapse measurements of Etd uptake in $CD4^+$ T lymphocytes under control conditions (white circles) or after 5 min (E) or 72 h (F) of exposure to $HIV_{ADA}$ (black circles). No differences were observed between R5 and X4 isolates. *p<0.005 denotes significance as compared to control conditions. Each value corresponds to mean±SD of the Etd intracellular intensity present in at least 20 cells per time point, n=4.

The invention provides a method of treating a mammalian subject having an HIV infection, or suspected of having been exposed to HIV, comprising administering to the mammalian subject an amount of (i) an inhibitor of a purinergic receptor, or (ii) an antagonist of a Panx1 hemichannel, effective to inhibit (a) HIV fusion with a target cell, or (b) HIV replication, or (c) HIV entry into a target cell, or two or more of (a), (b) and (c).

In an embodiment, the inhibitor of a purinergic receptor is administered. In an embodiment, the inhibitor is a purinergic P2X$_1$, P2X$_7$ and P2I$_1$ receptor inhibitor. In an embodiment, the inhibitor is a selective P2X$_1$ receptor inhibitor. In an embodiment, the inhibitor is a selective P2X$_1$ receptor inhibitor and does not substantially inhibit P2X$_7$ or P2Y$_1$, in an embodiment, the inhibitor inhibits HIV entry into a target cell. In an embodiment, the target cell is a macrophage.

In an embodiment, the antagonist or inhibitor inhibits HIV entry into a target cell. In an embodiment, the antagonist or inhibitor inhibits HIV replication.

In an embodiment, the target cell is a macrophage. In an embodiment, the target cell is a CD4+ lymphocyte. In an embodiment, the target cell is a CD4+. In an embodiment, the target cell is a CCR5+ and CXCR4+ cell.

In an embodiment, the inhibitor is MRS 2179 (2'-deoxy-N6-methyladenosine 3',5'-bisphosphate tetrasodium salt), NF449 (4,4',4'',4'''-[Carbonylbis(imino-5,1,3-benzenetriyl-bis(carbonylimino))]tetrakis-1,3-benzenedisulfonic acid, octasodium salt), PPNDS (Pyridoxal-5'-phosphate-6-(2'-naphthylazo-6'-nitro-4',8'-disulfonate)tetrasodium salt), or Ro 0437626 (N-[(1R)-2-[[(1S,2R,3S)-1-(Cyclohexylmethyl)-3-cyclopropyl-2,3-dihydroxypropyl]amino]-2-oxo-1-(4-thiazolyttnethyl)ethyl]-1H-benzimidazole-2-carboxamide). In an embodiment, the purinergic receptor inhibitor inhibits P2X$_1$ at a greater potency than it inhibits all other purinergic receptors.

In an embodiment, the inhibitor is oxidized ATP (oATP) (such as periodate-oxidized), NF 279 (8,8'-[Carbonylbis(imino-4,1-phenylenecarbonylimino-4,1-phenylenecarbonylimino)]bis-1,3,5-naphthalenetrisulfonic acid hexasodium salt, or A-740003 (N-[1-[[(Cyanoamino)(5-quinolinylamino)methylene]amino]-2,2-dimethylpropyl]-3,4-dimethoxybenzeneacetamide), A 839977 (1-(2,3-Dichlorophenyl)-N-[[2-(2-pyridinyloxy)phenyl]methyl]-1H-tetrazol-5-amine), AZ 10606120 dihydrochloride (N-[2-[[2-[(2-Hydroxyethyl)amino]ethyl]amino]-5-quinolinyl]-2-tricyclo[3.3.1.13,7]dec-1-ylacetamide dihydrochloride), AZ 11645373 (3-[1-[[3'-Nitro[1,1'-biphenyl]-4-yl)oxy]methyl]-3-(4-pyridinyl)propyl]-2,4-thiazolidinedione), MRS 2279 ((1R*,2S*)-4-[2-Chloro-6-(methylamino)-9H-purin-9-yl]-2-(phosphonooxy)bicyclo[3.1.0]hexane-1-methanol dihydrogen phosphate ester diammonium salt), or MRS 2500 tetraammonium salt ((1R*,2S*)-4-[2-Iodo-6-(methylamino)-9H-purin-9-yl]-2-(phosphonooxy)bicyclo[3.1.0]hexane-1-methanol dihydrogen phosphate ester tetraammonium salt), AZD9056, CE-224535, EVT-401, brilliant blue G R250 or brilliant blue G G250

In an embodiment, the selective P2X$_1$ receptor inhibitor has nanomolar antagonist potency at a human P2X$_1$ receptor for example, an IC$_{50}$ of 10 nM or less, or 1 nM or less. In an embodiment, the selective P2X$_1$ receptor inhibitor having nanomolar antagonist potency at a human P2X$_1$ receptor has no antagonist activity at other purinergic receptors or has antagonist activity at other purinergic receptors of substantially less than nanomolar antagonist potency, for example an IC$_{50}$ of 1 µM or more. A non-limiting example of such is a (4,4',4'',4'''-[Carbonylbis(imino-5,1,3-benzenetriyl-bis(carbonylimino))]tetrakis-1,3-benzenedistilfonic acid salt, such as an octasodium salt. In an embodiment, the selective P2X$_1$ receptor inhibitor is a reversible competitive antagonist at the P2X$_1$ receptor. In a preferred embodiment, the P2X$_1$ receptor is a human P2X$_1$ receptor.

In an embodiment, the antagonist of a Panx1 hemichannel is administered. In an embodiment, the antagonist of a Panx1 hemichannel comprises $^{10}$Panx (WRQAAFVDS; SEQ ID NO:1).

In an embodiment, the method comprises administering a plurality of inhibitors comprising at least an inhibitor each of purinergic receptors P2X$_1$, P2X$_7$ and P2I$_1$.

In an embodiment, the mammalian subject is a human.

In an embodiment, the subject is further administered an additional anti-HIV therapy. Anti-HIV therapies are well-known in the art.

In an embodiment, the subject has not previously been administered a purinergic P2X$_1$, P2X$_7$ and P2I$_1$ receptor inhibitor, as applicable.

Also provided is an assay method for identifying a purinergic receptor inhibitor or Panx1 antagonist as a candidate treatment for an REV infection, comprising experimentally determining HIV replication in an HIV-infected cell under conditions permissive of HIV replication and contacting the HIV-infected cell with the purinergic receptor inhibitor or Panx1 antagonist and experimentally determining HIV replication in the cell under the conditions permissive of HIV replication in the presence thereof, and identifying the purinergic receptor inhibitor or Panx1 antagonist as a candidate treatment for an HIV infection, wherein a reduction in, or inhibition of, HIV replication in the HIV-infected cell in the presence of the purinergic receptor inhibitor or Panx1 antagonist as compared to HIV replication in the HIV-infected cell in the absence of the purinergic receptor inhibitor or Panx1 antagonist, respectively, indicates that the purinergic receptor inhibitor or Panx1 antagonist is a candidate treatment for HIV infection.

Also provided is an assay method for identifying a purinergic receptor inhibitor or Panx1 antagonist as a candidate treatment for preventing or inhibiting HIV infection in a mammalian subject or reducing the likelihood of HIV infection, comprising experimentally determining HIV entry into, or fusion with, a target cell, under conditions permissive of HIV entry into, or fusion with, a target cell and contacting the HIV-infected cell with the purinergic receptor inhibitor or Panx1 antagonist and experimentally determining HIV entry into, or fusion with, a target cell under the conditions permissive of HIV entry into, or fusion with, the target cell in the presence thereof, and identifying the purinergic receptor inhibitor or Panx1 antagonist as a candidate treatment for preventing or inhibiting HIV infection in a mammalian subject or reducing the likelihood of HIV infection, wherein a reduction in, or inhibition of HIV replication in the HIV-infected cell in the presence of the purinergic receptor inhibitor or Panx1 antagonist as compared to in the absence of the purinergic receptor inhibitor or Panx1 antagonist, respectively, indicates that the purinergic receptor inhibitor or Panx1 antagonist is a candidate treatment for preventing or inhibiting HIV infection or reducing the likelihood of HIV infection.

In an embodiment of the assay methods, the Panx1 antagonist is a small organic molecule of less than 2000 daltons or a peptide of 20 amino acids or less or an antibody or fragment of an antibody or an siRNA or a nucleic acid. In an embodiment of the assay methods, the Panx1 antagonist is a small organic molecule of less than 1500 daltons. In an embodiment of the assay methods, the Panx1 antagonist is a small organic molecule of less than 1000 daltons. In an embodiment of the assay methods, the Panx1 antagonist is a small organic molecule of less than 1000 daltons. In an embodiment of the assay methods, the purinergic receptor inhibitor is a P2X$_1$, P2X$_7$ or P2I$_1$ receptor inhibitor and is a small organic molecule of less than 2000 daltons or a peptide of 20 amino acids or less or an antibody or fragment of an antibody or an siRNA or a nucleic acid. In an embodiment of the assay methods, the $P2X_1$, $P2X_7$ or $P2I_1$ receptor inhibitor is a small organic molecule of less than 1500 daltons. In an embodiment of the assay methods, the $P2X_1$, $P2X_7$ or $P2I_1$ receptor inhibitor is a small organic molecule of less than 1000 daltons. In an embodiment of the assay methods, the $P2X_1$, $P2X_7$ or $P2I_1$ receptor inhibitor is a small organic molecule of less than 500 daltons. In an embodiment of the assay methods, the target cell is a CCR5+, CXCR4+ cell. In an embodiment of the assay methods, the target cell is CD4+. In an embodiment of the assays, the target cell is a mammalian cell. In an embodiment of the assay methods, the target cell is a human cell. In an embodiment of the assay methods, the target cell is a macrophage. In an embodiment of the assay methods, the target cell is a CD4+ T lymphocyte.

Also provided is a purinergic $P2X_1$, $P2X_7$ and $P2I_1$ receptor inhibitor for treatment of an HIV infection or for inhibition or prevention of an HIV infection.

Also provided is a Panx1 hemichannel antagonist for treatment of an HIV infection or for inhibition or prevention of an HIV infection.

As used herein, the term "antibody" refers to complete, intact antibodies. As used herein "antibody fragment" refers to Fab, Fab', F(ab)2, and other antibody fragments, which fragments (like the complete, intact antibodies) bind the antigen of interest, in this case a Panx1 or a $P2X_1$, $P2X_7$ and $P2I_1$ receptor, as applicable.

Complete, intact antibodies, as used herein, include, but are not limited to, monoclonal antibodies such as murine monoclonal antibodies, polyclonal antibodies, chimeric antibodies, human antibodies, recombinant antibodies and humanized antibodies.

Various forms of antibodies may be produced using standard recombinant DNA techniques (Winter and Milstein, Nature 349: 293-99, 1991). For example, "chimeric" antibodies may be constructed, in which the antigen binding domain from an animal antibody is linked to a human constant domain (an antibody derived initially from a non-human mammal in which recombinant DNA technology has been used to replace all or part of the hinge and constant regions of the heavy chain and/or the constant region of the light chain, with corresponding regions from a human immunoglobulin light chain or heavy chain) (see, e.g., Cabilly et al., U.S. Pat. No. 4,816,567; Morrison et al., Proc. Natl. Acad. Sci. 81: 6851-55, 1984). Chimeric antibodies reduce the immunogenic responses elicited by animal antibodies when used in human clinical treatments. In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobulin light or heavy chain. That is, they are chimeras comprising mostly human immunoglobulin sequences into which the regions responsible for specific antigen-binding have been inserted (see, e.g., PCT patent application WO 94/04679). Animals are immunized with the desired antigen, the corresponding antibodies are isolated and the portion of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in antibodies for use in human therapies, and are less likely to elicit unwanted immune responses. Primatized antibodies can be produced similarly.

Another embodiment of the antibodies employed in the compositions and methods of the invention is a human antibody, which can be produced in nonhuman animals, such as transgenic animals harboring one or more human immunoglobulin transgenes. Such animals may be used as a source for splenocytes for producing hybridomas, as is described in U.S. Pat. No. 5,569,825.

Antibody fragments, e.g. of anti-Panx1 antibodies, and univalent antibodies may also be used in the methods and compositions of this invention. Univalent antibodies comprise a heavy chain/tight chain dimer bound to the Fc (or stem) region of a second heavy chain. "Fab region" refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as $F(ab)_2$), whether any of the above are covalently or non-covalently aggregated, so long as the aggregation is capable of specifically reacting with a particular antigen or antigen family.

The antibody can be, e.g., any of an IgA, IgD, IgE, IgG, or IgM antibody. In an embodiment the antibody is an immunoglobulin G (IgG). In an embodiment the antibody fragment is a fragment of an immunoglobulin G. In an embodiment the antibody is an IgG1, IgG2, IgG2a, IgG2b, IgG3 or IgG4. The IgA antibody can be, e.g., an IgA1 or an IgA2 antibody. A combination of any of these antibodies subtypes can also be used. One consideration in selecting the type of antibody to be used is the desired serum half-life of the antibody. IgG has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000). Another consideration is the size of the antibody. For example, the size of IgG is smaller than that of IgM allowing for greater penetration of IgG into tumors.

As used herein, the term "bind", or grammatical equivalent, means the physical or chemical interaction between two proteins or compounds or associated proteins or compounds or combinations thereof, including the interaction between an antibody and a protein. Binding includes ionic, non-ionic, hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences, but not an antibody obtained from a human or produced in a human. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies as defined herein isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

In an embodiment, the siRNA (small interfering RNA) as used in the methods or compositions described herein comprises a portion which is complementary to an mRNA sequence encoded a mammalian, preferably a human, Panx1, and the siRNA is effective to inhibit expression of Panx1. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding Panx 1. In another embodiment, a siRNA of the invention comprises a double-stranded RNA wherein one strand of the RNA comprises a portion having a sequence the same as a portion of 18-25 consecutive nucleotides of an RNA transcript of a gene encoding Panx1. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length. In yet another embodiment, a siRNA of the invention is 46 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In embodiments of the invention, the agent to be assayed or to be used in the present methods of treatment is a short hairpin RNA ("shRNA"). The shRNA is introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, in the present case Panx1. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs, in an embodiment the overhangs are UU.

In embodiments of the invention, the agent to be assayed or to be used in the present methods of treatment is an aptamer. As used herein an "aptamer" is a single-stranded oligonucleotide or oligonucleotide analog that binds to a particular target molecule, such as a Panx1, or to a nucleic acid encoding a Panx1, and inhibits the function or expression thereof, as appropriate. Alternatively, an aptamer may be a protein aptamer which consists of a variable peptide loop attached at both ends to a protein scaffold that interferes with Panx1 protein interactions.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Here, it is disclosed that the interaction of CD4 and CCR5 and/or CXCR4 is crucial for the biphasic Panx1 hemichannel opening induced by HIV in human primary CD4+ T lymphocytes. It is also disclosed that chemokines that bind CCR5 and CXCR4 increase Panx1 hemichannel activity, but only early, and more transiently, as compared to the biphasic opening of Panx1 hemichannels in response to HIV infection. Down-regulation or pharmacological blockade of Panx1 hemichannels inhibited HIV replication in CD4+ T lymphocytes, demonstrating that the opening of these channels is essential for HIV replication.

HIV infection of primary human PBMCs and CD4+ T lymphocytes induces opening of Panx1 hemichannels, but not of Cx43 hemichannels: To identify whether HIV induces hemichannel opening in PBMCs and CD4+ T lymphocytes, the effect of two R5 viruses (HIVADA and HIVBal, 20 ng/ml and 0.001 MOI, respectively) and one X4 virus (HIVLAI, 20 ng/ml) was evaluated by measuring the rate of uptake of ethidium (Etd, 5 µM). Ethidium only crosses the plasma membrane in healthy cells by passing through specific large channels, such as Cx and Panx hemichannels, and its intracellular fluorescence is reflective of channel opening (18, 21). The results indicated that HIVADA induced an early and transient (~5-30 min) increase in Etd uptake rate that returned near to baseline levels at approximately 30 min and remained at that level for the following 24 h in PBMCs and CD4+ T lymphocytes (FIGS. 1A and B). At 48 h, the Etd uptake rate increased, reaching maximal values at 72 h, which was subsequently maintained or gradually decreased to control values up to 120 h, the last time point assayed, depending on the viral isolate used (FIGS. 1A and B). In addition, both HIVBal and HIVLAI induced similar responses of Etd uptake in response to HIV infection in PBMCs (not shown) and CD4+ T lymphocytes (FIGS. 1C and D). HIVBal is a purified virus that lacks cytokines and other factors released that may be present in HIV stock supernatants. Thus, the data indicate that HIV, and no contaminant from the virus isolation process, induced the hemichannel opening. No significant changes in Etd uptake were detected in uninfected cells (FIG. 1A-D). Representative examples of Etd uptake in single experiments at 5 min (FIG. 1E) or after 72 h (FIG. 1F) of HIVADA exposure are shown.

Figures 2A, 2B, 2C, 2D, 2E, 2F:
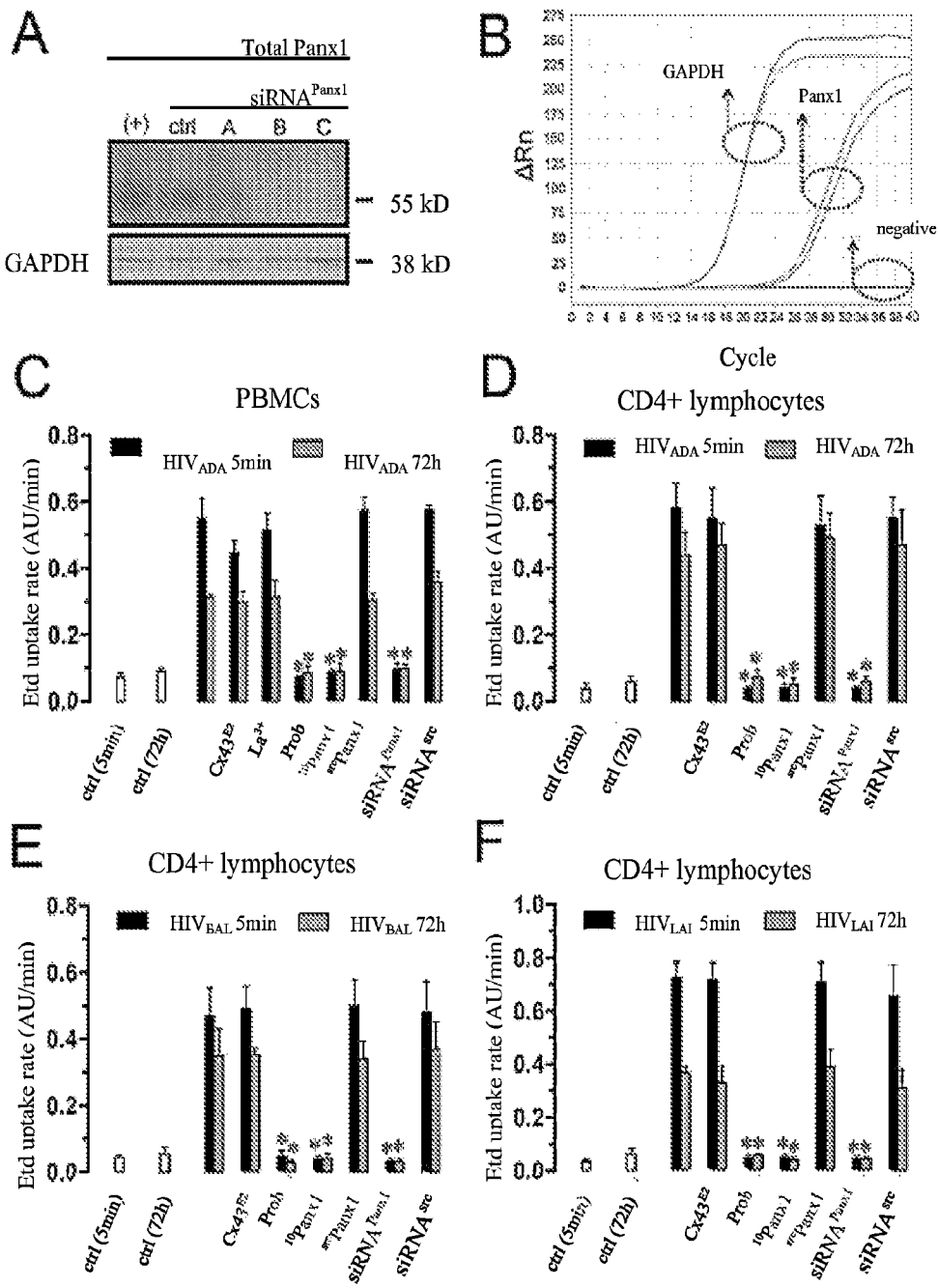
FIG. 2A-2F. HIV increases the activity of Panx1 hemichannels in human primary $CD4^+$ T lymphocytes, (A) Total levels of Panx1 in $CD4^+$ T lymphocytes under control conditions (Ctrl) or after transfection for 48 h with three different siRNA to Panx1 hemichannels (named siRNA A, B and C) were analyzed by western blot. HeLa cells transfected with Panx1 were used as a positive control of Panx1 protein expression (+). Loading controls, analyzed by probing for GAPDH, are also shown. (B) Representative example of qRT-PCR curves of panx1 mRNA expression in control (cyan line) and after transfection of siRNA to Panx1 (light green line). GAPDH was used as a control (yellow and red). The negative control without enzyme did not show any amplification (dark red line), (C-D) Etd uptake rate for PBMCs exposed to $HIV_{ADA}$ (C); $CD4^+$ T lymphocytes exposed to $HIV_{ADA}$ (D), $HIV_{Bal}$ (E) or $HIV_{LAI}$ (F) after 5 min (black bars) or 72 h (gray bars). (C-F) Control uninfected conditions are shown in white bars, (C-F) Addition of Cx43 hemichannel blockers $Cx43^{E2}$ (1:500 dilution) and lanthanum ($La^{3+}$, 200 μM) did not cause changes in Etd uptake induced by the virus. In contrast, Panx1 hemichannel blockers probenecid (Prob, 500 μM) and $^{10}$Panx1 (200 μM) completely blocked Etd uptake induced by the virus. The negative control using a scrambled $^{scr}$Panx1 peptide (200 μM) did not affect Etd uptake induced by the virus. (C-F) Cells were transfected with siRNA C for Panx1 or with the appropriate scramble siRNA (both 10 nM) and Etd uptake was analyzed, siRNA for Panx1, but not scramble control reduced Etd uptake induced by the virus. Each value corresponds to mean±SD of the Etd intracellular intensity present in at least 20 cells per time point, n=4 * represents significance of p<0.005.

To identify whether Panx1 hemichannels are involved in the HIV-induced Etd uptake in PBMCs and CD4+ T lymphocytes, Panx1 protein expression was down-regulated using siRNA. Three siRNA to Panx1 were tested (siRNA named A, B and C) by transfection of CD4+ T lymphocytes as described in the material and methods. Each siRNA reduced Panx1 protein expression as determined by Western blot (FIG. 2A). The siRNA C to Panx1 was the most effective in reducing Panx1 protein expression in CD4+ T lymphocytes (FIG. 2A). Thus, siRNA C to Panx1 was used in the subsequent experiments. qRT-PCR experiments confirmed that transfection of siRNA C into CD4+ T lymphocytes reduced Panx1 mRNA expression from a CT value of 12.3±0.7 cycles in control conditions to a CT of 23.5±2.5 cycles after transfection of siRNA C (FIG. 2B). Amplification of GAPDH as a loading control did not show any significant alterations in CT values, as values for control conditions were 16.7±0.2 and after Panx1 siRNA transfection were 16.9±0.2 (FIG. 2B, n=3). Based upon the kinetics of Panx1 hemichannel opening in response to HIV, we selected two representative time points of the early and late events of opening to perform blocking experiments (5 min and 72 h). Knockdown of Panx1 using siRNA in PBMCs and CD4+ T lymphocytes reduced the Etd uptake rate induced by HIVADA (FIGS. 2C and D), HIVBal (FIG. 2E) and HIVLAI (FIG. 2F) almost to undetectable control levels (uninfected cells) at the two representative time points, 5 min and 72 h (FIG. 2C-F). Panx1 scrambled siRNA did not alter the HIV induced increase in Etd uptake rate (FIG. 2C-F). To support further the involvement of Panx1 hemichannels in the HIV-induced Etd uptake, specific blockers against these channels were used. Two Panx1 hemichannel blockers, the mimetic peptide 10Panx1. (200 µM) and probenecid (Prob, 500 µM) (22, 23), completely reduced the HIVADA induced Etd uptake in PBMCs (FIG. 2C) and CD4+ T lymphocytes (FIG. 2D). Similar results were obtained when these blockers were used to inhibit the Etd uptake induced by HIVBal and HIVLAI in CD4+ T lymphocytes (FIGS. 2E and F). No toxic or nonspecific effects of these blockers alone were detected (data not shown). All these results indicate that Panx1 hemichannels are responsible for the HIV-induced Etd uptake in PBMCs and CD4+ T lymphocytes. In contrast, Lanthanum ($La^{3+}$), a general connexin hemichannel blocker, or Cx43E2, an antibody that blocks Cx43 hemichannels (18, 24, 25), did not affect the HIV induced Etd uptake rate (FIG. 2 C-F), suggesting that Cx43 hemichannels do not participate in this process.

Figures 3A, 3B, 3C, 3D, 3E:
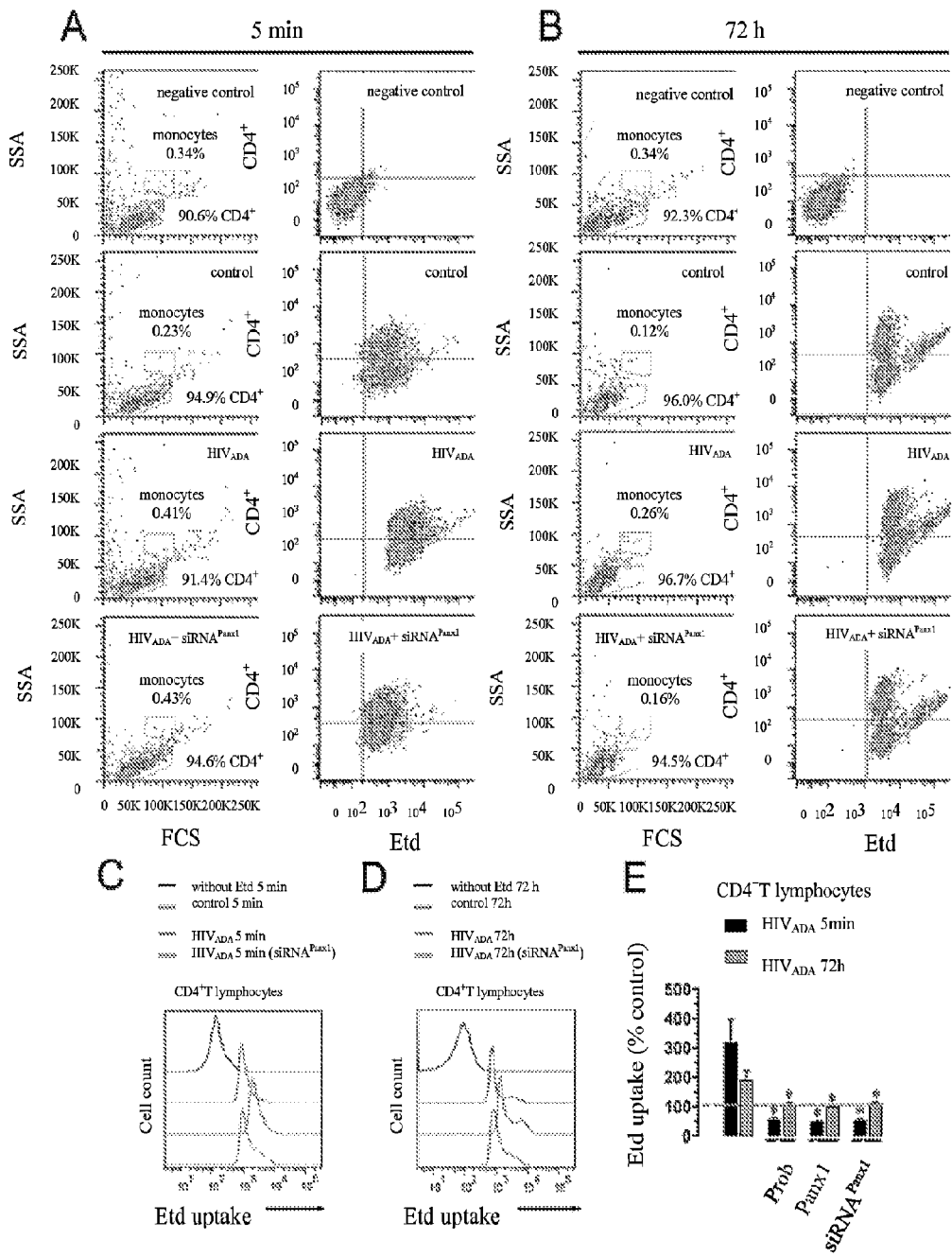
FIG. 3A-3E: HIV exposure/infection of $CD4^+$ T lymphocytes results in opening of Panx1 hemichannels as quantified by FACS. (A-B) FACS analysis showing Etd uptake in $CD4^+$ T lymphocytes after 5 min (A) or 72 h (B) of HIV exposure. Left panels in A and B show the Side scatter (SSA) versus the forward scatter (FCS of the cells) to demonstrate the purity and selection of the $CD4^+$ population of lymphocytes, while the right panels correspond to the CD4 staining versus the Etd uptake for each condition. Unstained Etd conditions (negative control) showed no staining for Etd, whereas untreated cells (control) showed minimal Etd uptake as compared to $HIV_{ADA}$ treated cultures ($HIV_{ADA}$) for 5 min (A) or 72 h (B). Cells transfected with siRNA for Panx1 abolished the Etd uptake increase induced by the virus at both time points (A and B, $HIV_{ADA}$+ $siRNA^{Panx1}$, respectively). (C and D) Representative histograms of FACS staining using no stained cells (without Etd, black lines), control conditions with Etd (red lines), after exposure to $HIV_{ADA}$ (blue lines) or after $HIV_{ADA}$+ $siRNA^{Panx1}$ (green lines). (E) Quantification of data from 3 independent experiments using FACS analysis showing that blocking of Panx1 hemichannels with probenecid (Prob), $^{10}$Panx1 or $siRNA^{Panx1}$ reduced Etd uptake induced by $HIV_{ADA}$ in $CD4^+$ T lymphocytes. Each value corresponds to mean±SD of the Etd intracellular intensity present in at least 20 cells per time point, n=4 * represents significance of p<0.005.

FACS analyses was also used to demonstrate that HIV induces Panx1 hemichannel activity in CD4+ T lymphocytes. FACS analyses were performed on CD4+ T lymphocytes used for Etd uptake and live cell imaging for 5 min and 72 h post HIVADA exposure. The first column of FIGS. 3A and B, corresponds to dot blots representing the purity and populations of cells analyzed at both time points (FIGS. 3 A and B). The second column represents the CD4 and Etd staining at both time points. HIVADA infection of CD4+ T lymphocytes showed a prominent Etd uptake in all cells at 5 min (FIG. 3 A, HIVADA) and 72 h (FIG. 3B, HIVADA) as compared to uninfected cells (FIGS. 3A and B, control cells) or non Etd treated cells (FIGS. 3A and B, negative control). Moreover, the increase in Etd uptake induced by the exposure to HIVADA (FIGS. 3A and B, HIVADA) was blocked by Panx1 siRNA (FIGS. 3A and B). Histogram analyses after 5 min (FIG. 3C) and 72 h (FIG. 3D) post infection (FIG. 3C and respectively) summarize the data showed in the dot blots. FIG. 3E summarizes all the data obtained using Etd uptake analyzed by FACS. HIV infection increased Etd uptake (representative time points are shown, 5 min and 72 h) in a Panx1 hemichannel dependent manner in CD4+ T lymphocytes. Blockers of Panx1 hemichannel, including Probenecid (Prob), [10]Panx1 and siRNA reduced to control conditions (100%) lad uptake induced by the virus at both time points (FIG. 3E).

Figures 4A, 4B, 4C, 4D, 4E, 4F:
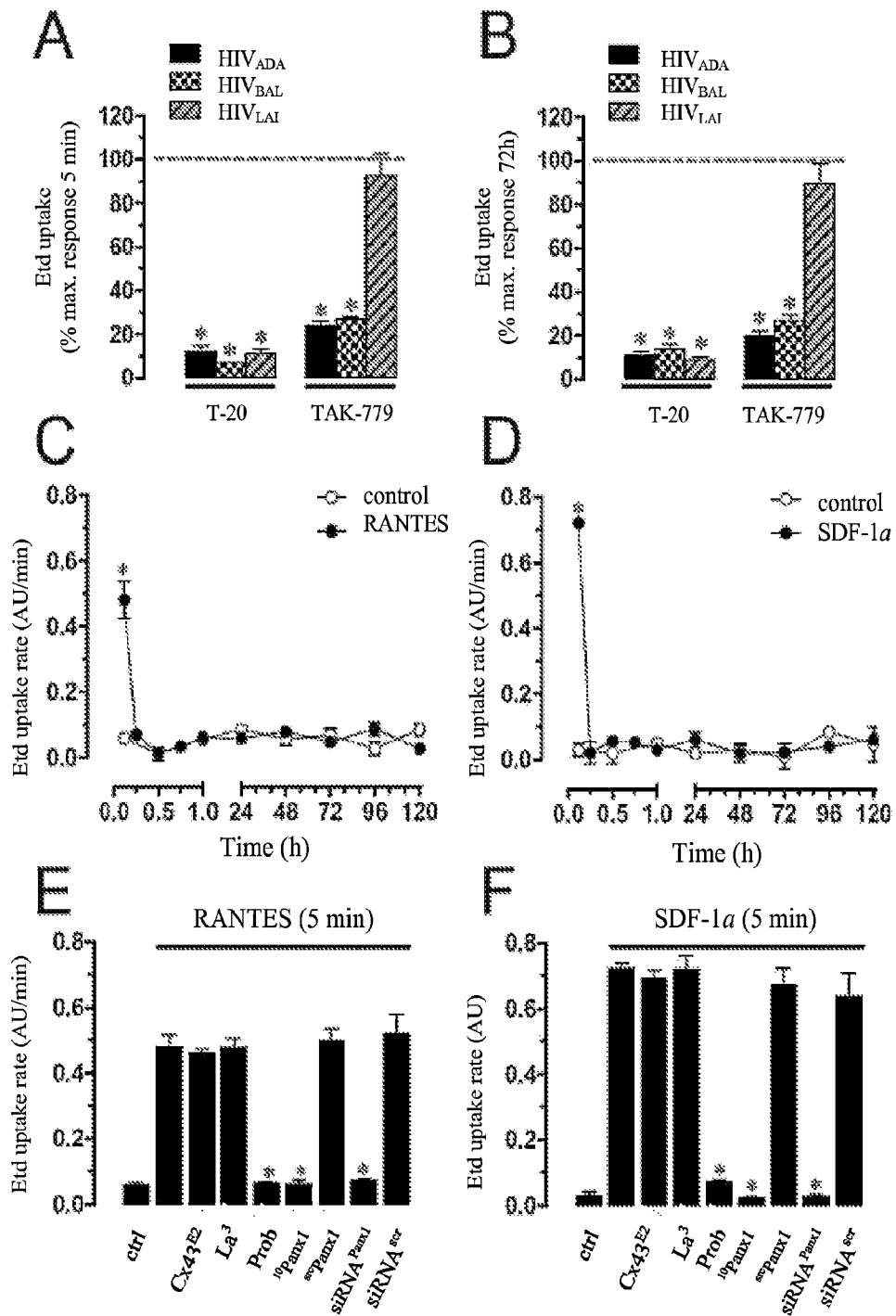
FIG. 4A-4F. The HIV-induced Panx1 hemichannel opening occurs by a CD4 and a CCR5/CXCR4-dependent mechanism. Effects of CD4 (T-20) and CCR5 blockers (TAK-779) on Etd uptake induced by $HIV_{ADA}$ (black bars), $HIV_{Bal}$ (squared pattern bars) and $HIV_{LAI}$ (angle stripe bars) infection at 5 min (A) and 72 h (B) of exposure. Data are presented as % of maximal response of Etd uptake (% max. response). (C, D) Etd uptake rate obtained from $CD4^+$ T lymphocytes under control conditions (white circles) or after a single addition of the follow chemokines (back circles): RANTES/CCL5 (C) or SDF-1α/CXCL12 (D). (E, F) The effects on Etd uptake of the Cx43 hemichannel Mockers $Cx43^{E2}$ (1:500 dilution) and $La^{3+}$ (200 μM) or Panx1 hemichannel blockers probenecid (Prob, 500 μM), $^{10}$Panx1. (200 μM), siRNA to Panx1 as well as negative controls scrambled peptide to $^{scr}$Panx1 (200 μM) or scrambled siRNA are shown (E and F, represent 5 min and 72 h post viral infection, respectively), * represent significance of p<0.005. Each value corresponds to mean±SD of Etd intracellular intensity in at least 20 cells per time point, n=4 for all experiments.

Binding of HIV to its cellular receptors, CD4 and CCR5 or CXCR4, results in opening of Panx1 hemichannels in CD4+ T lymphocytes: HIV entry into immune cells is dependent upon viral tropism mediated by interaction of the viral envelope with CD4 and CCR5 and/or CXCR4. To evaluate whether binding of the virus to its receptors is required for opening of Panx1 hemichannels, Etd uptake experiments were performed in human CD4+ T lymphocytes exposed to HIVADA (CCR5 dependent), HIVBal (CCR5 dependent) or HIVLAI (CXCR4 dependent) in the presence and absence of CD4 or CCR5 receptor blockers. Trimeris/T-20 (Roche, obtained from the AIDS NIH repository, 1 µg/ml), a blocker of viral fusion mediated by CD4 receptors in CD4+ T lymphocytes, inhibited the Etd uptake induced by all three viruses tested at 5 min and 72 h post infection (FIGS. 4A and B). Additionally, TAK-779 [(100 ng/ml, (26)], a potent inhibitor of HIV's binding to its co-receptor CCR5 (27), reduced the Etd uptake induced by WV R5 (HIVADA and HIVBal), but not the X4 virus (HIVLAI) (FIGS. 4A and B). These results demonstrate that the HIV-induced Panx1 hemichannel activity requires the binding of the virus to CD4 as well as to its corresponding chemokine receptor.

Binding of chemokines to the receptors CCR5 or CXCR4 results in transient Panx1 hemichannel opening: To examine whether chemokines that bind CCR5 or CXCR4 also induce opening of Panx1 hemichannels, a time course of Etd uptake, as described in FIG. 1, was performed. Addition of RANTES/CCL5 (100 ng/ml), a physiological ligand for CCR5, resulted in a fast and extremely transient increase (only 5 min) of Etd uptake in CD4+ T lymphocytes (FIG. 4C) as compared to HIV exposure. However, HIV maintained the opening of Panx1 hemichannel for a longer time, up to 30 min, as compared to the chemokines (compare to FIG. 1), suggesting a different mechanism of opening. Similar results were obtained for MIP-1α/CCL3 (100 ng/ml) and MIP-1β/CCL4 (100 ng/ml), both ligands for CCR5 (data not shown). In addition, the chemokine ligand for CXCR4, SDF-1α/CXCL12 (100 ng/ml), induced a similar transient increase in Etd uptake (FIG. 4D) as occurred with RANTES (FIG. 4C). However, no chemokine treatment reproduced the later stages of Etd uptake induced by HIV infection (FIGS. 4C and D, as compared to FIG. 1). The increase in Etd uptake induced by chemokines in CD4+ T lymphocytes was reduced by Panx1 hemichannels blockers, but not by Cx43 hemichannel blockers, in a similar manner as seen for HIV infection (FIGS. 4E and F). Negative controls using scrambled peptides or scrambled siRNA did not alter the Etd uptake induced by these chemokines (FIGS. 4E and F). In addition, we found that the purified viral envelope protein gp1.20 (1 μg/ml) also induced a transient Etd uptake at 5 min. The gp120-induced Etd uptake was inhibited by using Probenecid, 10Panx1 and siRNAPanx1, demonstrating that Panx1 hemichannels are opened in response to gp120's binding. No effects of scramble peptides (srcPanx1) or siRNAscr were detected. These data indicate that all known physiological ligands for CCR5 and CXCR4 as well as a viral envelope protein increase Panx1 hemichannel opening in CD4+ T lymphocytes.

Figures 5A, 5B, 5C:
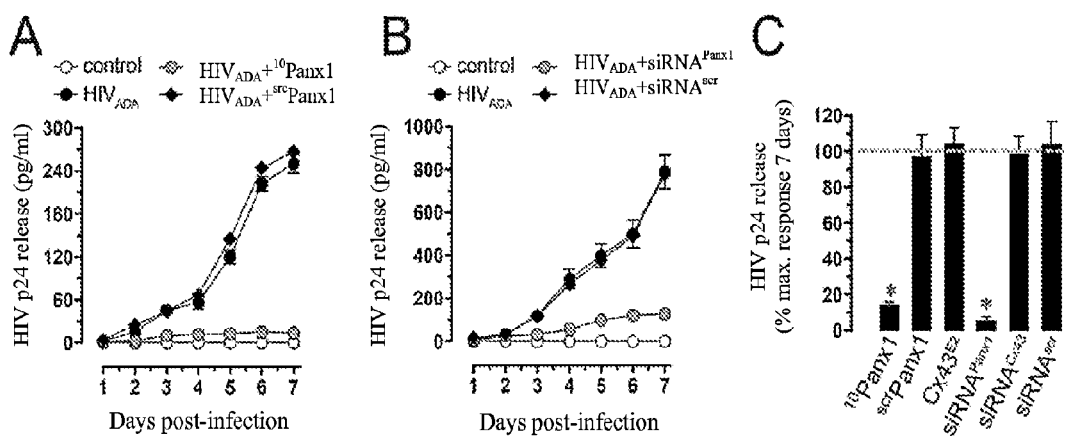
FIG. 5A-5C. Blockade of Panx1 hemichannels abolish HIV replication in $CD4^+$ T lymphocytes. (A-B) ELISA for HIV-p24 release in uninfected (white circles) or $HIV_{ADA}$ infected (black circles) $CD4^+$ T cells from two different donors. (A) Blockade of Panx1 hemichannels by using mimetic peptides ($^{10}$Panx1, 200 μM, gray circles) or (B) knockdown of Panx1 by using siRNA (gray circles, 10 nM) abolished HIV replication to almost control undetectable levels (white circles). Scrambled peptides and scrambled siRNA (black diamonds) did not alter viral replication. (C) Summary of 3 independent experiments after 7 days post infection of CD4+ T lymphocytes. HIV-p24 release into the media in the presence or absence of Cx43 hemichannel blocker Cx43$^{E2}$ (1:500 dilution) and the Panx1 hemichannel blocker $^{10}$Panx1 (200 µM) and scrambled peptide $^{scr}$Panx1 (200 µM) are shown. *represents significance of p<0.005. Each value corresponds to mean±SD of the Etd uptake intensity of at least 20 cells per time point, n=4 for all experiments.

Opening of Panx1 hemichannels in response to HIV infection is required for efficient HIV replication in CD4+ T lymphocytes: To examine whether opening of Panx1 hemichannels induced by HIV is required for viral replication in CD4+ T lymphocytes, we used the mimetic peptides $^{10}$Panx1 and siRNA to Panx1. These treated cells were then infected with HIVADA and viral replication was determined by HIV-p24 ELISA of supernatants collected each day for 7 days as previously described (17, 28, 29). Both $^{10}$Panx1 (200 μM) and the Panx1 siRNA dramatically reduced HIV replication in CD4+ T lymphocytes at all times tested (FIG. 5A-C). Negative controls using srcPanx1 or siRNAscr did not alter HIV replication (FIG. 5C). Thus, activation of Panx1 hemichannels in CD4+ T lymphocytes is essential for HIV infection and replication.

Discussion

The results demonstrate that HIV causes the opening of Panx1 hemichannels in a biphasic manner during infection of PBMCs and CD4+ T lymphocytes. The mechanism of Panx1 hemichannel opening in response to HIV involves the binding of the virus to its receptors CD4 and CCR5/CXCR4. It was also found that chemokines that bind CCR5 and CXCR4 as well as the recombinant viral envelope protein, gp120, resulted in a more transient opening of Panx1 hemichannels (only 5 min) as compared to the early opening of the channels in response to HIV infection (5-30 min). Chemokines and the recombinant viral envelope protein gp120 did not mimic the later events of Panx1 hemichannel opening (48 to 120 h). It was also demonstrated that Panx1 hemichannel opening is required for HIV replication in CD4+ T lymphocytes. Thus, Panx1 hemichannels are critical host proteins required for HIV infection and replication in CD4+ T lymphocytes.

HIV infects immune cells by binding of its envelope protein gp120 to host CD4 and then CCR5 and/or CXCR4 receptors, depending on the viral tropism (30-33). In addition to the well described binding of HIV to its receptors and viral fusion, signaling in response to binding of gp120 occurs, such as increased intracellular free $Ca^{2+}$ and G-protein signaling (2-4), and opening of nonselective cation channels and $Ca^{2+}$ activated $K^+$ channels (5). The identity of these non-selective cation channels remained unknown. It is apparent from the results that Panx1 hemichannels is one of these channels.

It was estimated that 4-6 CCR5 receptors and several CD4 receptors need to cluster together to bind several HIV envelope proteins to form a fusion pore (34, 35). Yet, the probability of several CD4 and CCR5 and/or CXCR4 molecules coming together naturally in the membrane is low, so there must be a cellular response that facilitates the formation of this fusion pore (36) by a mechanism that involves lipid rafts and actin rearrangements (37-39). It is likely that some of these functions are controlled by opening of Panx1 hemichannels in response to HIV exposure. Opening of Panx1 hemichannels results in changes in ionic gradients, as well as release of several factors, including ATP (11, 13, 18, 40). ATP is a regulator of the channel, but also is a signaling molecule that can activate purinergic and adenosine receptors in an autocrine and paracrine manner (41-44). In agreement, recently P2Y2 receptors have been implicated in HIV replication in T cell lines and PBMCs (6). All chemokines that bind CCR5 or CXCR4 opened Panx1 hemichannels transiently (only 5 min), whereas the time course of opening induced by the virus was longer, suggesting key differences in signaling and regulation of the gating of Panx1 hemichannels between HIV and chemokines. In agreement, calcium imaging studies demonstrated that HIV gp120 protein, as well as chemokines that bind CCR5 and CXCR4, elicit different calcium signaling, which likely depend upon binding characteristics to the respective chemokine receptors (5). The later events of activation of Panx-1 hemichannels and the molecules that induce this constant opening from 24 to 72 h post infection, are unknown. However, it is proposed that part of this Panx-1 hemichannel opening is mediated by the synthesis of new viral particles and subsequent infection of new and super infection of previously infected cells. These differences in signaling are unknown and warrant further investigation to dissect both mechanisms.

The proposed mechanism of how and when Panx1 hemichannels participate in HIV infection and replication in CD4+ T lymphocytes is that upon binding of the virus to its host cellular receptors, signaling occurs, mediated by CD4 and chemokine receptors. These signals result in opening of Panx1 hemichannels, resulting in changes in ionic gradients and release of second messengers, including ATP and its sub products that activate extracellular ATP, ADP and adenosine receptors, that ultimately signal to facilitate HIV infection of CD4+ T lymphocytes. However, it cannot be discounted, as described above, that Panx1 hemichannels also participate in recruitment of cellular receptors to areas of viral fusion.

Materials and Methods

Materials: RPMI medium, fetal bovine serum, penicillin/streptomycin, and trypsin-EDTA were purchased from GibcoBRL/Invitrogen (Carlsbad, Calif.). The HIV isolates, CXCR4 and CCR5 blockers, and blocking antibodies were obtained from the National Institutes of Health AIDS Research and Reference Reagent Program, Division of AIDS, MAID, National Institutes of Health (Germantown, Md.). All other reagents were purchased from Sigma-Aldrich (St. Louis, Mo.), unless otherwise designated.

Isolation of human PBMCs and CD4+ T lymphocytes. Anticoagulated blood was obtained from leukopacks obtained from the New York Blood Center as described before (16). PBMCs were isolated by under-layering with Ficoll-Paque (Amersham Bioscience, Uppsala, Sweden) according to the procedure described by the manufacturer. Purified PBMC used in these studies were ~10% monocytes and ~90% lymphocytes and other hematopoietic cells, as determined by incubation with premixed human CD45 and CD14 monoclonal antibodies conjugated to FITC and PE, respectively (1:50, Caltag Laboratories, Burlingame, Calif.), followed by fluorescence-activated cell sorter analysis (FACS) as we previously described (17). To obtain a pure population of CD4+ T lymphocytes, monocytes were removed from PBMCs by using CD14 coupled magnetic beads and subsequently CD4+ T lymphocytes were isolated with CD4 coupled magnetic beads (Stem Cell Technologies, Vancouver, BC, Canada).

HIV-infection and quantification of replication. Cell-free viral inocula were obtained from the National Institutes of Health AIDS Research and Reference Reagent Program. Three isolates were used: HIVADA, and HIVBal, two R5 isolates and HIVLAI, an X4 isolate, PBMCs and purified CD4+ T lymphocytes were isolated and activated with phytohemagglutinin (PHA; 5 µg/ml) plus interleukin (IL-2; 5%) in RPMI 1640 for 48 h in polypropylene tubes at a density of $2 \times 10^6$ cells/nit PBMCs and CD4+ T lymphocytes were then infected by incubation for 24 h with viral stocks of HIVADA (20 ng p24/ml/$1 \times 10^6$ cells), HIVLAI (20 ng p24/ml/$1 \times 10^6$ cells) or HIVBal (0.001 MOI), washed thoroughly, resuspended in fresh medium, and maintained in polypropylene tubes. Uninfected control cells were activated with PHA plus IL-2 for 48 h, washed, and maintained in polypropylene tubes in fresh media without any virus. To determine the levels of HIV infection, the amount of HIV-p24 released into the medium was determined by ELISA (PerkinElmer, Boston, Mass.)

Dye uptake and time lapse fluorescence imaging. To characterize the functional state of Panx1 hemichannels, dye uptake experiments using ethidium (Etd) bromide were performed as previously described (18, 19). Cells were washed twice in Hank's balanced salt solution and then exposed to Locke's solution (containing: 154 mM NaCl, 5.4 mM KCl, 2.3 mM CaCl2, 5 mM HEPES and pH 7.4) with 5 µM Etd and time lapse microscopy was performed. Phase-contrast and fluorescence microscopy with time-lapse imaging were used to record cell appearance and fluorescence intensity changes in each condition. Fluorescence was recorded every 30 s. The NIH ImageJ program was used for off-line image analysis and fluorescence quantification. For data representation and calculation of Etd uptake slopes, the average of two independent background fluorescence intensity measurements (FB, expressed as arbitrary units, AU) was subtracted from fluorescence intensity' in each cell (F1). Results of this calculation (F1-FB), for at least 20 cells, were averaged and plotted against time (expressed in minutes). Slopes were calculated using Microsoft Excel software and expressed as AU/min. Microscope and camera settings remained the same in all experiments. Dead cells were clearly identified during the time lapse microscopy due to their non specific Etd uptake (not inhibited by hemichannel blockers) and were not quantified.

Flow cytometry. To measure Etd uptake in CD4+ T cell populations FACS analysis was performed of cells under control conditions or after HIV exposure at several time points. Etd uptake experiments were performed in CD4+ lymphocytes ($3-5 \times 10^5$), and after the respective time of Etd uptake, cells were fixed with 2% paraformaldehyde for 30 min at room temperature, incubated with 1% BSA in PBS for 30 min and stained with CD4 antibody for 30 min at 4° C. For analyses of Etd positive populations, 10,000 events were acquired on a BD FACS Canto II and analyzed using FlowJo (Ashland, Oreg.) software as we previously described (17, 20).

siRNA and peptides. Three unique 27mer siRNA duplexes against human Panx1 were predesigned and obtained from Origen (Rockville, Md.). siRNA (10 nM) transfection was performed with Oligofectamine (Invitrogen) according to the Origene application guide for Trilencer-27 siRNA and minimal cell death was detected after transfection. Experiments were carried out 2 days post transfection. The Panx1 mimetic blocking peptide $^{10}$Panx1 (WRQAAFVDSY) (SEQ ID NO:1) and the scramble peptide (FADRYWAQVS) (SEQ ID NO:2) were synthesized by Peprotech, NJ.

Quantitative RT-PCR: Cultured CD4+ T lymphocytes ($2 \times 10^6$ cells/ml in 5 ml) were transfected with oligofectamine (Invitrogen, Inc) containing siRNA A, B and C (Origene, Rockville, Md.) for 2 days as described above. Total RNA was extracted using TRizol (Invitrogen, Carlsbad, Calif.) and phase lock system (eppendorf Inc.) following manufacturer instructions. cDNA sysnthesis was performed using 2 µg of total RNA using iSript cDNA Synthesis Kit (Biorad, Hercules, Calif.) according to the manufacturer's instructions. The amplified cDNA was used to amplify and quantify GAPDH and Panx1 mRNA expression by quantitative PCR using ABsolute Blue qPCR SYBR low ROX mix in a StepOne Plus Thermocycler (ABI). The primers used correspond to GAPDH Forward: 5'-GAGAAGIATGACAACAGCCICAA-3' (SEQ ID NO:3), GAPDH Reverse: 5'-AGTCCTTCCACGATACCAAAG-3' (SEQ ID NO:4), PANX1 Forward: 5'-AGAAGAATGC-CCGACAGAGA-3' (SEQ ID NO:5), PANX 1 Reverse: 5'-TTGCAAACCAGCTGTGAAAC-3' (SEQ ID NO:6). The program used was denaturation for 15 min at 95° C. and 40 cycles of denaturation, 15 s at 95° C., anneal 30 s at 60° C. and amplification, 30 s at 72° C. Expression was determined using the $\Delta\Delta CT$ method (ABI) according to the CT values.

Statistical Analysis. Student's two-tailed, paired T test was used to compare the different groups. A value of $p<0.005$ was considered significant.

Example 2

Figures 6A, 6B, 6C, 6D:
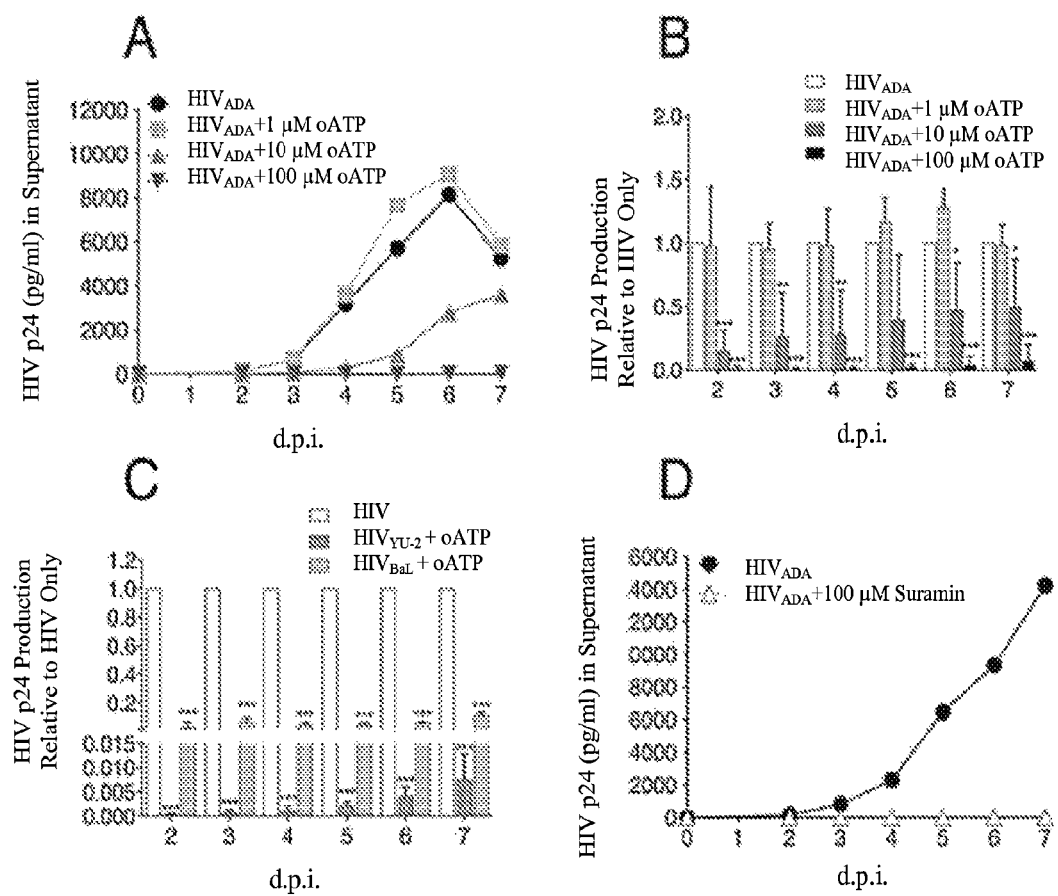
FIG. 6A-6D. Blocking P2 receptors inhibits HIV replication in a dose-dependent manner. This inhibition is independent of viral strain. Primary human macrophages were inoculated with 2 ng/nil of HIV$_{ADA}$ (A, B, D), 0.2 ng/ml HIV$_{BaL}$, or 2 ng/ml HIV$_{YU-2}$ (C) in the presence or absence of oxidized ATP (oATPA, A-C), a. P2X receptor inhibitor, or suramin (D), a non-specific general P2X and P2Y antagonist, for 24 hours. Supernatants were collected and fresh oATP or suramin added every 24 hours until 7 days post inoculation (d.p.i.). HIV p24 levels in the supernatant were determined by ELISA. (A) represents the replication curve for one representative donor infected with HIV$_{ADA}$. HIV p24 production with oATP relative to HIV only is summarized for multiple donors for HIV$_{ADA}$ (B, N=5 for 1 and 10 µM oATP, N=10 for 100 µM oATP), HIV$_{BaL}$, or HIV$_{YU-2}$ (C, N=3, 100 µM oATP). (D) represents the replication curve for one representative donor infected with HIV$_{ADA}$ and treated with suramin. Three donors all showed 100% inhibition of replication with suramin at every time point tested. All values are given as the mean±SD. *p<0.05, p<0.01, *p<0.001 relative to HIV only.

Purinergic receptors are necessary for HIV replication in human macrophages: To determine whether purinergic receptors are required for HIV replication, primary human macrophages were infected with HIV in the presence or absence of the P2X receptor inhibitor oxidized ATP (oATP) and examined production of the viral capsid protein HIV p24 in the medium every 24 hours post inoculation. Oxidized ATP inhibits mainly $P2X_7$ as well as $P2X_1$ and $P2X_2$ receptors (72, 73). Treatment with 100 µM oATP significantly blocked HIV replication in macrophages up to 7 days post inoculation (d.p.i.), the last time point examined (FIG. 6A, representative donor). Thus, studies were focused on these purinergic receptors. This effect was consistent in 10 donors tested despite donor variability in the amount of HIV p24 produced (J. E. Hazleton, J. W. Berman, and E. A. Eugenin, unpublished data). Treatment with 100 μM oATP did not reduce cell viability as determined by a live/dead cell assay (see Materials and Methods).

Inhibition of HIV replication was independent of viral strain, as treatment of macrophage cultures with 100 μM oATP significantly inhibited replication of three different R5-tropic strains, $HIV_{ADA}$, $HIV_{BaL}$, and $HIV_{YU-2}$ (FIG. 6B, N=10, FIG. 6C, N=3). $HIV_{ADA}$ replication was reduced 92-99% depending upon the d.p.i. (*p<0.0001 at every d.p.i. relative to HIV only, FIG. 1B), $HIV_{BaL}$ replication was reduced 89-97% (*p<0.001-0.0005, relative to HIV only and according to the respective d.p.i, FIG. 6C), and for $HIV_{YU-2}$, oATP reduced replication by over 99% on every d.p.i. (***p<0.001 at every d.p.i. relative to HIV only, FIG. 6C). The inhibition of replication with oATP treatment for each donor was dose dependent, with 10 μM oATP inhibiting $HIV_{ADA}$ p24 production to a lesser extent than 100 μM, 50-85% inhibition relative to HIV only depending upon d.p.i. (p=0.0004-0.04, FIG. 6B), and 1 μM oATP showing no effect (FIGS. 6A and 6B). Treatment with suramin, a non-specific general P2X and P2Y antagonist, inhibited $HIV_{ADA}$ replication by 100% (FIG. 6D, N=3) without altering cell viability (see Materials and Methods). Thus, purinergic receptors are required for HIV replication in primary human macrophages.

Figures 7A, 7B, 7C, 7D:
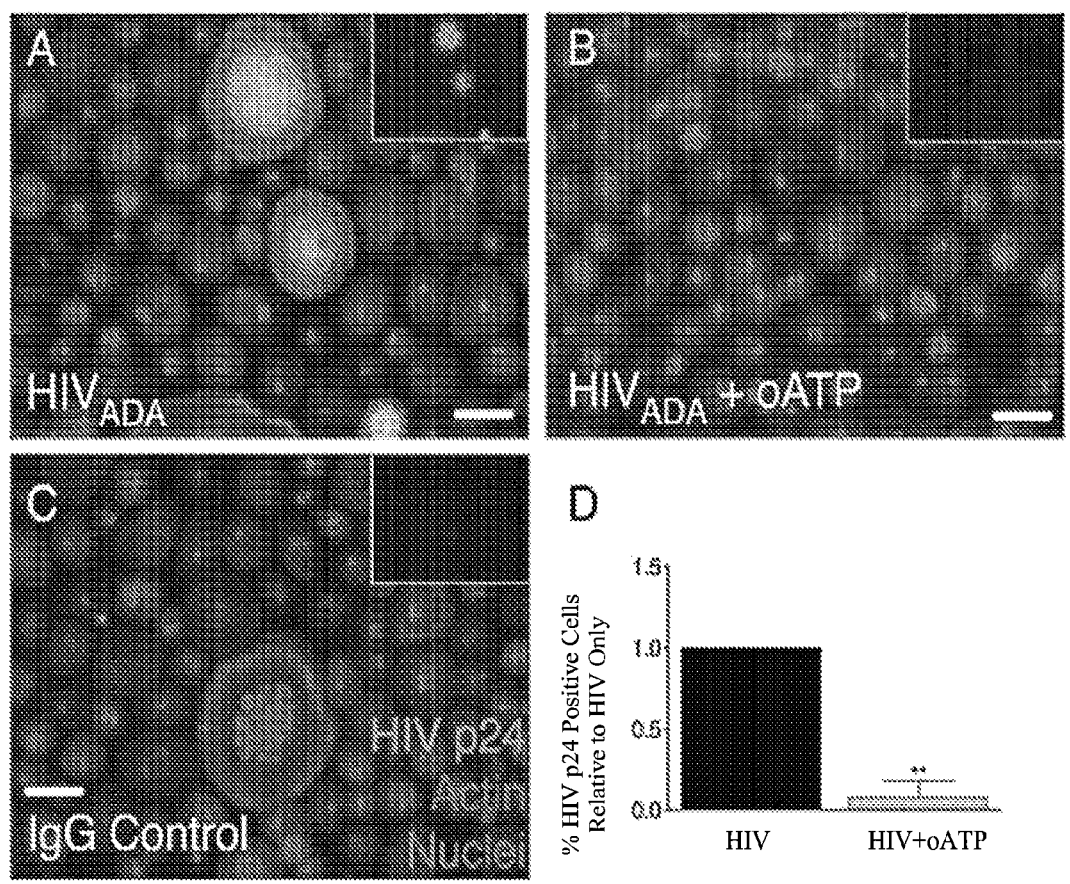
FIG. 7A-7D. Inhibition of P2 receptors decreases the percentage of HIV infected cells. Primary human macrophages were inoculated with 20 ng/ml HIV$_{ADA}$ (A, C) or 20 ng/ml HIV$_{ADA}$ and 100 µM oATP (B) for 24 hours. The cells were washed and medium with fresh oATP was replaced every 24 hours until 7 d.p.i., when the cells were fixed and permeabilized and stained for actin (phalloidin-Texas Red, red), nuclei (DAPI, blue), and HIV p24 (A,B) or mouse IgG$_1$ control (C) (FITC, green). Images were taken of 15 fields per condition and percentage of HIV p24 positive cells was determined by counting the number of nuclei with green cytoplasmic staining relative to total number of nuclei. Results are shown as the mean±SD (D). **p=0.0037 relative to HIV only, N=3, scale bar=50 µM, inset=green channel only FIG. 8A-8B. P2X$_1$, P2X$_7$, and P2Y$_1$ receptors mediate HIV replication. We focused on these three receptors based on our oATP, BBG and suramin data. Primary human macrophages were inoculated with 2 ng/ml. HIV$_{ADA}$ in the presence or absence of antagonists. Supernatants were collected every 24 hours post inoculation and viral replication was determined by HIV p24 ELISA. Treatment with 100 µM NF 279, a P2X$_1$ antagonist, and MRS 2179, a P2Y$_1$ antagonist, significantly reduced viral replication relative to HIV only. Treatment with 100 µM A-740003, a P2X$_7$ antagonist, significantly reduced viral replication relative to HIV plus DMSO (A-740003 vehicle). All blockers were titered to select the optimal concentration that was in the specific range of each reagent. (A) Representative replication curve for One donor. (B) Summary of fold change reduction in viral replication for multiple donors (N=3). All values are given as the mean±SD. *p<0.05, p<0.01, *p<0.001 as compared to HIV only or HIV plus DMSO (A-740003).

Inhibition of purinergic receptors decreases the percentage of HIV-infected macrophages: To determine whether the reduction in viral replication with purinergic receptor antagonists was due to a decrease in the number of cells infected with HIV or to a decreased release of virus from the same number of infected cells, macrophages were infected for 7 days in the presence or absence of oATP (100 μM), stained for HIV p24 (green, FITC), actin (red, phalloidin-Texas Red), and nuclei (blue, DAPI), and examined by fluorescence microscopy. In the $HIV_{ADA}$ infected cultures we detected positive intracellular HIV p24 staining and frequent formation of multinucleated giant cells (FIG. 7A, $HIV_{ADA}$), which result from fusion of HIV-infected cells (74). Inhibition of purinergic receptors with oATP resulted in a significant 92% decrease in the percentage of HIV p24 positive cells and very few multinucleated giant cells were detected in these cultures as compared to HIV infected cultures (FIG. 7B, $HIV_{ADA}$+oATP). HIV p24 positive cells were quantified by counting the percentage of nuclei in cells with green cytoplasmic staining relative to total number of nuclei. Data from 2 additional donors were quantified and are illustrated in FIG. 7D (N=3, **p=0.0037 $HIV_{ADA}$+oATP relative to HIV only). The use of an $IgG_1$ negative control antibody in HIV infected cultures did not result in any non-specific staining (FIG. 7C, IgG Control).

Figures 8A, 8B:
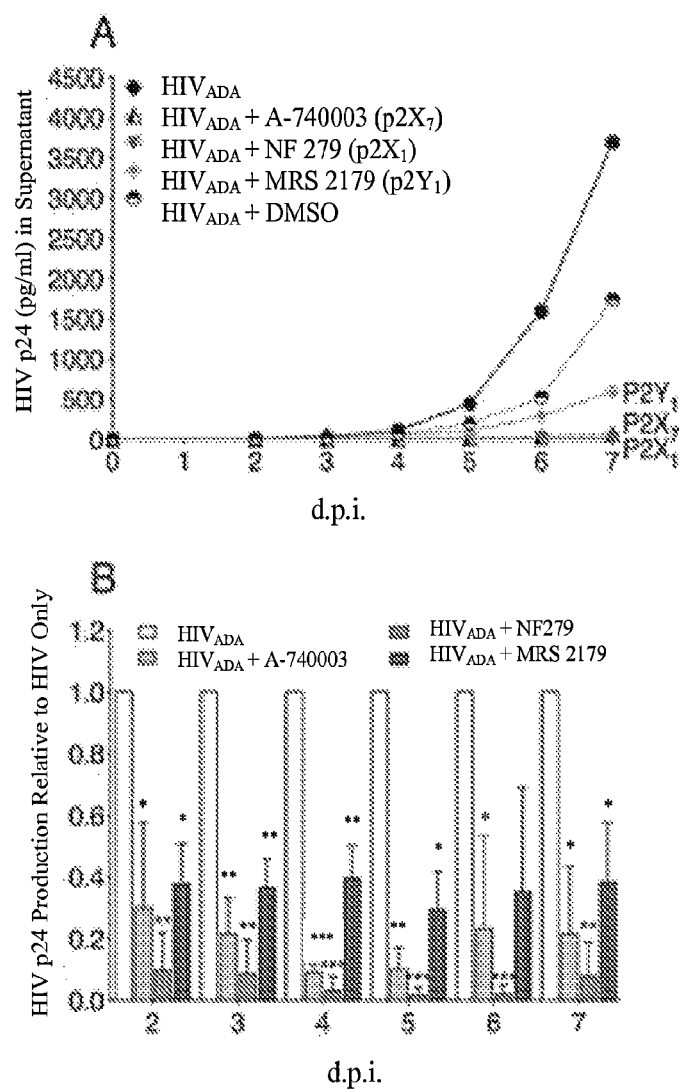

$P2X_1$, $P2X_7$, and $P2Y_1$ purinergic receptors participate in HIV replication in macrophages. Macrophages express $P2X_1$, $P2X_4$, $P2X_7$, and $P2Y_1$, $P2Y_2$, $P2Y_4$, $P2Y_6$, and $P2Y_{12}$ receptors (20, 21). The combined data obtained using oATP, that mostly inhibits $P2X_1$, $P2X_2$ and $P2X_7$ (28, 29), BBG, a specific $P2X_7$ antagonist, and suramin, a general P2X and P2Y inhibitor, focused the research on $P2X_1$ and $P2X_7$ receptors. Also examined were $P2Y_1$ receptors as they have been identified in macrophages. Additionally, western blot analyses indicated that macrophages expressed all of these purinergic receptors in control and HIV infected conditions (data not shown). To determine the purinergic receptors involved in HIV replication in macrophages, the following specific pharmacologic P2 receptor antagonists were used: NF 279, a specific $P2X_1$ antagonist, A-740003, a specific $P2X_7$ antagonist, and MRS 2179, a specific $P2Y_1$ antagonist. At 100 μM, all three inhibitors significantly reduced viral replication (FIG. 8A, representative donor). As described in the materials and methods different concentrations of these antagonists were tested, at concentrations that were described to mediate specific effects on purinergic receptors. Inhibition was dose-dependent, with 100 μM resulting in the greatest inhibition. Treatment with 100 μM NF 279, A-740003, or MRS 2179 did not alter cell viability during the time course analyzed (see Materials and Methods). Quantification of viral replication from macrophages isolated from 3 independent donors indicated that NF 279 resulted in 90-98% inhibition of HIV p24 production on days 2-7 post inoculation and MRS 2179 inhibited HIV p24 production 60-70% as compared to HIV infected cultures without the inhibitors (FIG. 8B). The $P2X_7$ antagonist A-740003 inhibited HIV p24 production 70-91% relative to HIV plus the vehicle DMSO (FIG. 8B). Also examined was another $P2X_7$ specific antagonist, brilliant blue G (BBG), which has been tested in mice as a potential therapeutic for spinal cord injury in humans (75). BBG treatment of macrophage cultures infected with HIV inhibited viral replication 54-90% relative to cultures infected with HIV only. Therefore, at least three purinergic receptors, $P2X_1$, $P2X_7$, and $P2Y_1$, are required for HIV replication in macrophages.

Figures 9A, 9B, 9C, 9D:
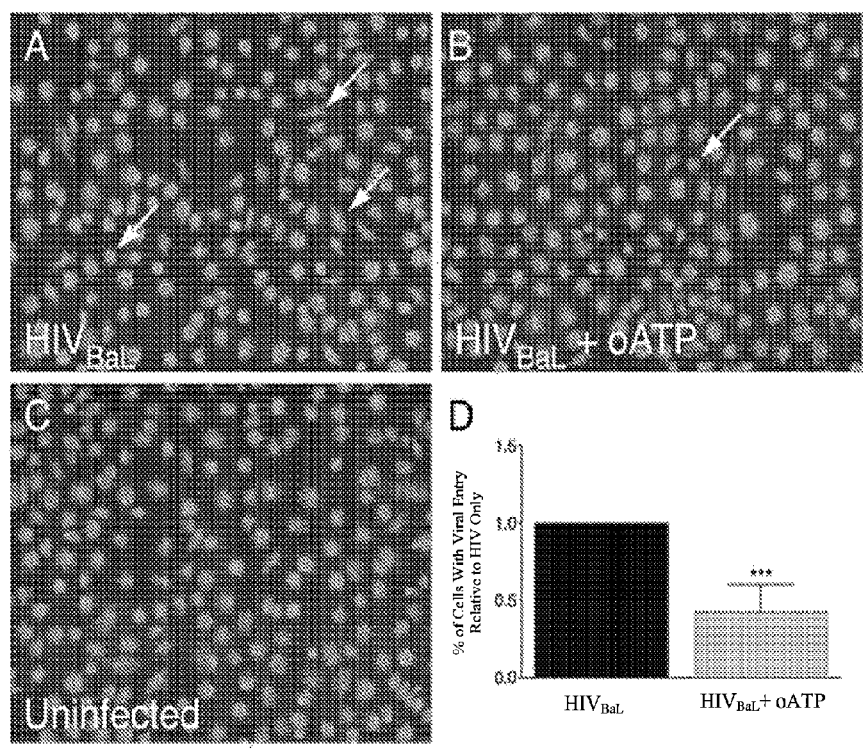
FIG. 9A-9D. P2 receptors participate in HIV entry into primary human macrophages. Macrophages were inoculated with β-lactamase containing HIV$_{BaL}$ at an MOI of 0.001-0.01 for 4 hours in the absence (A) or presence of 100 µM oATP (B) followed by loading with CCF2-AM, which fluoresces green (excitation 409 nm, emission 520 nm). When viral entry occurs, β-lactamase cleavage of CCF2-AM results in blue fluorescence (excitation 409 nm, emission 447 nm, representative cells indicated by arrows). The percentage of cells with viral entry decreased 57% with oATP treatment (D). There was no non-specific blue fluorescence detected in uninfected control cells (C). Percentage of cells with viral entry in the presence of oATP relative to HIV only is shown as mean±SD. ***p=0.0009, N=5

Purinergic receptors are required for HIV entry into macrophages. To determine whether purinergic receptors are required for viral entry, we examined the effect of oATP on HIV entry into human macrophages. Macrophages were inoculated with β-lactamase containing viral particles and loaded with CCF2-AM, which fluoresces green, but when cleaved by β-lactamase the molecule fluoresces blue. Therefore, in this assay cells into which HIV entered fluoresce blue while all other cells are green. The percentage of viral entry was determined by assessing the number of Hue cells relative to the total number of cells. HIV infection of macrophages for 4 hours with β-lactamase containing $HIV_{BaL}$ resulted in 4-30% viral entry depending upon the donor (FIG. 9A, representative donor). When cells were inoculated with β-lactamase containing $HIV_{BaL}$ in the presence of the purinergic receptor blocker oATP (100 μM), there was a reduction in viral entry (FIG. 9B, representative donor). Quantification of HIV entry into macrophages from 5 independent donors indicated that oATP significantly reduced viral entry by 57% (FIG. 9D, ***p=0.0009 relative to HIV only). In uninfected cultures, there were no blue cells, indicating no non-specific blue fluorescence (FIG. 9C). The majority of our previous experiments were performed using $HIV_{ADA}$. However, entry assays were not performed with $HIV_{ADA}$ because there is no molecular clone of this strain, which would be required for the production of β-lactamase containing viral particles.

Figures 10A, 10B, 10C, 10D, 10E, 10F, 10G, 10H, 10I:
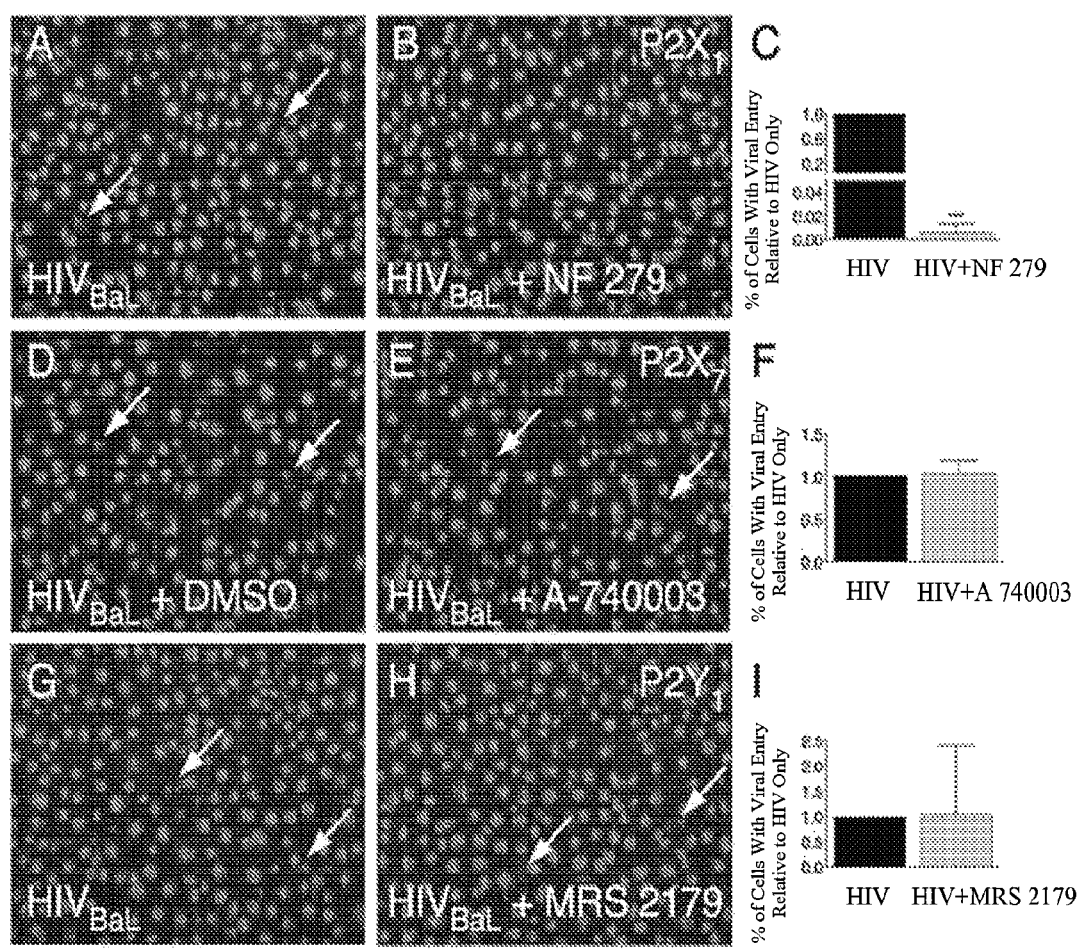
FIG. 10A-10I, P2X$_1$ receptors are necessary for HIV entry into primary human macrophages. Macrophages were inoculated with β-lactamase containing HIV$_{BaL}$ at an MOI of 0.001-0.005 for 4 hours in the absence (A, D, G) or presence of 100 µM NF 279, a P2X$_1$ antagonist (B), 100 µM A-740003, a P2X$_7$ antagonist (E), or 100 µM MRS 2179, a P2Y$_1$ antagonist (H). Viral inoculation was followed by loading the cells with CCF2-AM, which fluoresces green. When viral entry occurs, β-lactamase cleavage of CCF2-AM results in blue fluorescence. The percentage of cells with viral entry significantly decreased 98% with NF 279 treatment (C). Viral entry did not change with A-740003 (F) or MRS 2179 (1) treatment. Percentage of cells with viral entry in the presence of antagonist relative to HIV only is shown as mean±SD. ***p<0.0001, N=3

$P2X_1$ receptors, but not $P2X_7$ or $P2Y_1$ receptors, facilitate HIV entry: To determine whether the purinergic receptors $P2X_1$, $P2X_7$, and/or $P2Y_1$ that facilitate viral replication participate in viral entry, we used the β-lactamase HIV entry assay to examine HIV entry into macrophages in the presence of 100 μM NF 279, a $P2X_1$ antagonist, A-740003, a $P2X_7$ antagonist, and MRS 2179, a $P2Y_1$ antagonist. Concomitant treatment with the $P2X_1$ antagonist resulted in a 98% reduction in $HIV_{BaL}$ entry (FIG. 10A-C, N=3, ***p<0.0001). Neither the $P2X_7$ antagonist (FIG. 10D-F, N=3) nor the $P2Y_1$ antagonist (FIG. 10G-I, N=3) inhibited viral entry despite the fact that $P2X_7$ antagonism resulted in a 70-91% reduction in viral replication and $P2Y_1$ antagonism resulted in 60-70% inhibition of replication (FIG. 8B). This suggests that $P2X_1$ participates in viral entry, while $P2X_7$ and $P2Y_1$ regulate later stages of the viral life cycle.

Figures 11A, 11B, 11C:
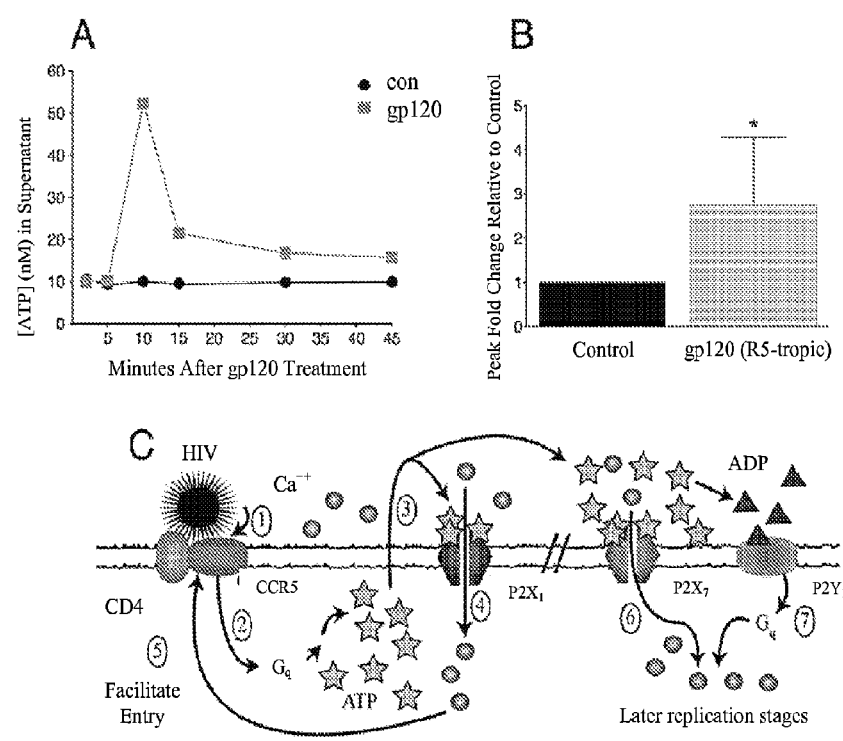
FIG. 11A-11C. HIV gp120 induces an increase in ATP release from primary human macrophages. Cells were inoculated with 20-60 nM monomeric R5-tropic gp120$_{BaL}$, (N=2) or gp120$_{SF162}$ (N=4) for 2, 5, 10, 15, 30 and 45 minutes. ATP levels in the supernatant were quantified using a luminescence assay. ATP concentration increased at 5, 10, or 15 minutes depending upon the donor used. (A) ATP release for one representative donor with peak ATP release at 5 minutes. Fold change in ATP release was calculated for the time when there was maximal increase. (B) Peak fold change in ATP release is shown as mean±SD. HIV gp120 significantly increased ATP release 1.8 fold. *p=0.0387, N=8. As a positive control, mechanical stress (repeated pippeting of media) to the macrophage cultures was used, (C) Proposed model for purinergic receptor involvement in HIV replication. HIV's binding to CD4 and CCR5 (1) induces signaling (2), potentially through Gα$_q$ proteins that lead to ATP release (3). Extracellular ATP binds to and activates P2X$_1$ receptors, causing calcium influx (4) that facilitates HIV entry (5). ATP release continues and over time enough ATP accumulates to activate P2X$_7$ receptors leading to further calcium influx and downstream signaling events that facilitate later stages in the HIV life cycle (6). With time, ATP will also be converted to ADP, activating P2Y$_1$ receptors, which may signal through Gα$_q$ to increase intracellular calcium and cause signaling that facilitates later stages in the HIV life cycle (7).

HIV gp120 induces ATP release from macrophages: It was demonstrated that purinergic receptors play an important role in HIV replication, and $P2X_1$ receptors regulate HIV entry into macrophages. Activation of these receptors requires binding by an extracellular ligand such as ATP. To determine whether HIV's binding to CD4 and CCR5 on macrophages directly stimulates ATP release, levels of extracellular ATP were measured following treatment with HIV gp120, the surface protein that initiates viral binding and fusion. ATP in the supernatant was quantified using a chemiluminescent assay. Treatment of primary human macrophage cultures with gp120 (SF162 or BaL, 20-60 nM, both CCR5-tropic) resulted in a significant increase in ATP release (FIG. 11A, representative donor with an increase in ATP release at 10 minutes). No significant release was detected before 5 minutes of treatment. Peak ATP release always occurred within 5-15 minutes of gp120 treatment, depending upon the donor. A 1.8 fold increase in ATP release with gp120 treatment was detected for the peak response time to gp120 relative to vehicle treated cultures (FIG. 11B, N=8, *p=0.0387).

Thus, it is likely that HIV's binding to CD4 and CCR5 results in an autocrine release of ATP. This extracellular ATP binds to $P2X_1$ receptors, resulting in signaling that is necessary for HIV entry into macrophages (see proposed model, FIG. 11C). Other purinergic receptors, including $P2X_7$ and $P2Y_1$, likely participate in later stages of the viral life cycle and may be activated following accumulation of ATP or conversion of ATP to ADP (FIG. 11C). Activation of these receptors requires ADP or higher levels of extracellular ATP.

Discussion

Herein is demonstrated a novel function for purinergic receptors as necessary mediators of HIV replication in macrophages. Selective $P2X_1$, $P2X_7$, and $P2Y_1$ antagonists all blocked viral replication, but only the $P2X_1$ antagonist inhibited viral entry. $P2X_7$ and $P2Y_1$ receptors likely participate in later stages of the viral life cycle. It was also demonstrated that gp120's binding to primary human macrophages results in local ATP release within 5-15 minutes, facilitating an autocrine activation of purinergic receptors.

There are three classes of purinergic receptors, P1, adenosine receptors, and P2X and P2Y, ATP receptors. P2X (1-7) receptors are ligand-gated cation channels, predominantly resulting in increased calcium flux from the extracellular space. P2Y (1-12) receptors are G-protein coupled. The majority of P2Y receptor subtypes signal through $IP_3$ to cause an increase in intracellular calcium levels from intracellular stores (63). A role for $P2X_1$, $P2X_7$, and $P2Y_1$ receptors was identified in participating in HIV replication. Each of these receptors participates in inflammation and the host response to pathogens. $P2X_1$ receptors facilitate neutrophil chemotaxis, increasing neutrophil recruitment to sites of inflammation, and participate in thrombin-induced platelet activation (76, 77). $P2Y_1$ receptors are required for inflammatory hyperalgesia, *Chlamydia pneumoniae*-induced platelet aggregation, and chemokine secretion by keratinocytes (78-80). $P2X_7$ receptors have a wide range of inflammatory functions including cytokine secretion, particularly IL-1β secretion, cell to cell fusion, and superoxide formation (66-68, 81). $P2X_7$ receptors also regulate the host response to *Toxoplasma gondii, Chlamydia trachomatis*, and *Mycobacterium tuberculosis* (82-84). Thus, the data indicate a novel role for P2 receptors in facilitating HIV replication.

It was shown that $P2X_1$ receptor is the predominant subtype required for HIV entry and that $P2X_7$ and $P2Y_1$ are involved in later stages of the viral life cycle. HIV entry involves binding of gp120 to host CD4 and subsequent conformational changes that enable binding to the co-receptor CCR5 or CXCR4. Binding of these proteins leads to fusion with the cell membrane at the cell surface or in some circumstances within an endosomal compartment. The role of other host cell proteins involved in viral entry is not well characterized, but studies indicate that viral binding initiates a signaling cascade that may be necessary for entry. Treatment of macrophages with HIV gp120 induces CCR5-dependent calcium influx (60, 62). Studies with cell lines indicate that gp120 signals through CCR5 to activate $G\alpha_q$ and initiate signaling involving phospholipase C, protein kinase C, Pyk2, and Ras (59). This signaling leads to Rac-1 mediated rearrangements in the actin cytoskeleton that facilitate membrane fusion and may be necessary for viral entry (59). It is demonstrated that signaling induced by gp120's binding also stimulates ATP release. It is likely that subsequent autocrine activation of $P2X_1$ receptors by extracellular ATP results in facilitation of infection.

It was demonstrated that an ATP release induced by gp120's binding to macrophages. The cellular mechanisms for ATP release in primary human macrophages have not been well characterized, but a number of potential mechanisms have been identified in other cell types. Pannexin and connexin hemichannels are proteins through which extracellular ATP is released in many cells including those of the immune system (86-89). Recently it was demonstrated in T cell lines release ATP through opening of pannexin-1 hemichannels upon HIV infection (90) or during cell to cell fusion (81). These large pore channels are activated by signals of cellular stress including increased intracellular calcium (91), which occurs in macrophages following gp120's binding. These hemichannels are likely activated following gp120's binding and may represent a conduit for ATP release. Other potential mechanisms of ATP release include voltage-dependent anion channels or exocytosis from ATP-containing vesicles (92).

Regardless of the mechanism, it appears that the initial ATP release that occurs with gp120's binding activates $P2X_1$, and that this receptor specifically mediates viral entry rather than $P2X_7$ and $P2Y_1$, which was also found to be involved in viral replication. $P2X_1$ is highly responsive to ATP, being activated by low nanomolar concentrations, whereas ATP is a relatively poor agonist at $P2X_7$, and ADP is the predominant agonist of $P2Y_1$ (49-51). Therefore, $P2X_1$ is likely activated initially by ATP while activation of the other receptors may be delayed, requiring an accumulation of ATP or its conversion to ADP by ectonucleotidases. In agreement, the apyrase data indicated no reduction in HIV entry or replication in macrophages. This may be due to the fact that apyrase breaks down ATP to ADP and subsequently to adenosine and all of these products also activate purinergic and adenosine receptors.

The findings that purinergic receptors are necessary for HIV entry and later stages in viral replication is therapeutically important. The nearly complete inhibition of viral replication by multiple purinergic receptor antagonists shows that these receptors are therapy targets. A number of purinergic receptor antagonists are already in animal model or human testing for treatment of neuropathic pain, inflammatory disease, and potentially depression (75, 96-99). Three $P2X_7$ receptor antagonists, AZD9056, CE-224535, and EVT-401, are in clinical trials for treatment of rheumatoid arthritis (98). Studies using oATP, which was found herein to be a potent inhibitor of HIV replication and of viral entry, in an in vivo mouse model demonstrated that it blocks purinergic receptors systemically and can prevent the onset of diabetes and inflammatory bowel disease (99). BBG, another antagonist that was shown to be an inhibitor of viral replication, has also been tested in vivo in a rat model of traumatic spinal cord injury. This study demonstrated recovery of motor function and limited inflammation following spinal cord injury without any toxicity of BBG (75).

Materials and Methods

Reagents: Oxidized ATP (oATP) and brilliant blue G (BBG) were from Sigma Aldrich (St. Louis, Mo.). A-740003, MRS 2179, NP 279, and suramin were from Tocris Bioscience (Ellisville, Mo.). To assure that the antagonists were used at the concentration that blocks purinergic receptors, we tested different concentrations of the inhibitors A-740003 (10, 50, 75 and 100 µM), MRS2179 (0.1, 1, 10 and 100 µM), NF279 (10, 50, 75 and 100 µM) and BBG (1, 10 and 100 µM). All concentrations were in the specific range of blocking as suggested (Tocris, Ellisville, Mo.). It was determined that 100 µM and lower concentrations of these antagonists reduced viral replication in macrophages. No toxic effect of these antagonists was observed in macrophages. Monomeric gp120$_{BaL}$ (R5-tropic) and the plasmids for β-lactamase virus production, pWT/Bat and pMM310 were from the NIH AIDS Research and Reference Reagent Program (Germantown, Md.). Monomeric gp120$_{SF162}$ (R5-tropic) was a generous gift from Dr. Leo Stamatatos (Seattle Biomedical Research Institute, Seattle, Wash.). RPMI 1640 and penicillin/streptomycin (P/S) were from Gibco/invitrogen (Grand island, NY). Human AB serum and PBS were from Lonza (Walkersville, Md.). HEPES was from USB (Cleveland, Ohio).

Monocyte isolation and macrophage culture: Human monocytes were isolated from leukopaks obtained from the New York Blood Center. Peripheral blood mononuclear cells (PBMCs) were isolated by differential centrifugation using a Ficoll gradient (GE Healthcare, Piscataway, N.J.) and CD14 positive cells were isolated from PBMCs using CD14 monoclonal antibodies that were then bound by magnetic nanoparticles and separated using a magnetic field (Stem Cell Technologies, Vancouver, BC, Canada). Isolated CD14 positive cells were cultured adherently for 6 days in the presence of 10 ng/ml macrophage-colony stimulating factor (PeproTech, Rocky Hill, N.J.) in RPMI 1640 with 10% FBS, 5% human AB serum, 1% P/S, and 10 mM HEPES to differentiate the cells into macrophages.

HIV replication: After 6 days in culture, macrophages in 48-well plates at a density of $10^5$ cells per well were inoculated with 2-20 ng/ml HIV$_{ADA}$, 2 ng/ml HIV$_{YU-2}$, or 0.2 ng/ml HIV$_{BaL}$ for 24 hours in the presence or absence of purinergic receptor inhibitors. 5 wells were inoculated per condition. After 24 hours, cells were washed with PBS and then cultured with media. Supernatants were collected and medium was changed every 24 hours until 7 days post inoculation (d.p.i.). When the inhibitors oATP, A-740003, MRS 2179, NF 279, BBG, or suramin, were used, they were added when the medium was changed every 24 hours. Viral replication was analyzed by HIV p24 ELISA (Advanced Bioscience Laboratories, Kensington, Md.) according to the manufacturer's instructions To determine whether any of the inhibitors used resulted in cell death, we assessed cell viability using a live/dead assay. Macrophages were grown in 35 mm MatTek (Ashland, Mass.) dishes at a density of $10^6$ cells per dish for 6 days and then treated with 100 µM of oATP, A-740003, MRS 2179, NF 279, BBG, or suramin for 24 hours. Cells were then washed with PBS and incubated with 4 µM Ethidium homodimer-1 (excitation 528 nm, emission 617 nm) and 0.5 µM Calcein AM (excitation 494 nm, emission 517 nm) for 30-45 minutes according to the manufacturer's instructions (LIVE/DEAD Viability/Cytotoxicity Kit, Invitrogen, Eugene, Oreg.). Cells were imaged using a Zeiss AxioObserver.D1 with an LD Plan-Neofluar 20×/0.4 air objective lens. Images were collected at room temperature through a Zeiss AxioCam MRm camera using Axiovision software. None of the antagonist caused any decrease in cell viability.

Immunofluorescence: After 6 days in culture, macrophages cultured in 35 mm MatTek dishes at a density of $10^6$ cells per dish were inoculated with 20 ng/ml HIV$_{ADA}$ for 24 hours in the presence or absence of oATP. Two MatTek dishes were inoculated per condition. After 24 hours, cells were washed with PBS and cultured with media. Fresh oATP was added and the medium was changed every 24 hours until 7 d.p.i. Cells were then fixed using cold 70% ethanol for 20 minutes. Cells were washed with PBS and blocked using 0.9% fish gelatin, 50 µM EDTA. 1% horse serum, and 1% globulin-free albumin. The following primary antibodies were used: mouse monoclonal HIV p24 antibody from Abcam at a 1:50 dilution (Cambridge, Mass.) or mouse myeloma IgG$_1$ (Sigma) as a negative control. Secondary antibody staining was with anti-mouse IgG F(ab)'$_2$ fragment conjugated to FITC (Sigma). Actin was stained using Texas Red-X conjugated to phalloidin (Invitrogen, Eugene, Oreg.). ProLong Gold antifade reagent containing DAPI was added to all cells to stain for nuclei. Cells were imaged using a Zeiss AxioObserver.D1 with an LD Plan-Neofluar 20×/0.4 air objective lens. Images were collected at room temperature through a Zeiss AxioCam MRm camera using Axiovision software. There was no image processing following image collection. Images for 15 fields per condition were analyzed and percentage of p24 positive cells determined by counting number of nuclei in cells with green cytoplasmic staining.

HIV Entry Assay: Primary human macrophages were cultured in black 96-well plates with a clear bottom (Corning Inc., Corning, N.Y.) at a density of 43,000 cells per well. After 7-8 days in culture, cells were inoculated with β-lactamase containing HIV$_{BaL}$ at a multiplicity of infection (MOI) of 0.01, 0.005, or 0.001 in the presence or absence of the purinergic receptor inhibitors oATP, NF 279, A-740003, or MRS 2179 for 4 hours. Beta-lactamase containing HIV$_{BaL}$ was generated as described previously (27). Briefly, HEK-293T cells were transfected using calcium phosphate with two plasmids, one containing the HIV$_{BaL}$ genome, pWT/BaL (NIH repository), the other containing β-lactamase fused to REV vpr, pMM310 (NIH repository). Cells were transfected for 16 hours and then supernatant was collected 24 and 48 hours following transfection. This resulted in production of complete viral particles containing active β-lactamase. Viral stocks were generated by sucrose gradient purification of the transfection supernatants.

Alter viral inoculation of primary human macrophages, cells were washed with phenol red-free DMEM (Gibco) then loaded with CCF2-AM for 6 hours at room temperature using the GeneBLAzer In Vivo Detection Kit (Invitrogen, Carlsbad, Calif.). CCF2-AM fluoresces green due to an internal fluorescence resonance energy transfer, but when cleaved by β-lactamase, this interaction is lost and the molecule fluoresces blue. Cells were imaged using an Olympus IX70 with a Plan 10×/0.25 air objective lens. Images were collected at room temperature through an Olympus E-620LS camera attached to the microscope through an OM adapter MF-1. Images were collected directly onto a memory card and there was no image processing following image collection. Images were collected for 8 fields in 4 separate wells per condition and percentage of cells positive for viral entry was determined by counting the number of blue cells (cells that virus had entered) as compared to the total number of blue and green cells.

ATP Release Assay: Macrophages were cultured in 96-well plates at a density of 30,000 to 43,000 cells per well. After 6-8 days in culture, medium was changed to phenol red-free RPMI 1640 with 1% P/S and 10 mM HEPES. Cells were then inoculated with media or 20-60 nM gp120$_{BaL}$ (N=2) or gp120$_{SF162}$ (N=4) for 2, 5, 10, 15, 30 and 45 minutes. Supernatants were collected and ATP concentrations were determined using the ATPlite luminescence assay system (Perkin Elmer, Waltham, Mass.) by combining 100 µl of sample with 100 µl of ATPlite reagent. Luminescence was measured using a GloMax 96 Microplate Luminometer (Promega, Madison, Wis.) or using an Envision plate reader (Perkin Elmer, Germany). The concentration of ATP released was determined by comparing sample luminescence to a standard curve of 0.39 to 100 nM ATP using the ATP standard provided by the manufacturer. As a positive control for ATP release, pippeting up or down, to activate mechanically the release of ATP, was performed.

Statistical analysis: Statistical analyses were used to determine significance of data from all experiments. Significance was assessed by determining the validity of the null hypothesis that states that all treated groups were the same as their respective controls, which were set to 1 (i.e. the null hypothesis was that the ratio of (HIV+treatment)/(HIV only)=1 or gp120 treated/untreated=1). GraphPad Prism software (version 5.0b) was used to test the null hypothesis by comparing the relative value to a theoretical mean of 1 using a two-tailed one sample t test with a 95% confidence interval.

REFERENCES

1. Melikyan, G. B. 2011. Membrane fusion mediated by human immunodeficiency virus envelope glycoprotein. *Curr Top Membr* 68:81-106,
2. Harmon, B., and L. Ratner. 2008. Induction of the Galpha(q) signaling cascade by the human immunodeficiency virus envelope is required for virus entry. *J Virol* 82:9191-9205.
3. Melar, M., D. E. Ott, and T. J. Hope. 2007. Physiological levels of virion-associated human immunodeficiency virus type 1 envelope induce coreceptor-dependent calcium flux. *J Virol* 81:1773-1785.
4. Weissman, D., R. L. Rabin, J. Arthos, A. Rubbert, M. Dybul, R. Swofford, S. Venkatesan, J. M. Farber, and A. S. Fauci. 1997. Macrophage-tropic HIV and SIV envelope proteins induce a signal through the CCR5 chemokine receptor. *Nature* 389:981-985.
5. Liu, Q. H., D. A. Williams, C. McManus, F. Baribaud, R. W. Doms, D. Schols, E. De Clercq, M. I. Kottikoff, R. O. Collman, and B. D. Freedman. 2000. gp120 and chemokines activate ion channels in primary macrophages through CCR5 and CXCR4 stimulation. *Proc Natl Acad Sci USA* 97:4832-4837.
6. Seror, C., M. T. Melki, F. Subra, S. Q. Raza, M. Bras, H. Saidi, R. Nardacci, L. Voisin, A. Paoletti, F. Law, I. Martins, A. Amendola, A. A. Abdul-Sater, F. Ciccosanti, O. Delelis, F. Niedergang, S. Thierry, N. Said-Sadier, C. Lamaze, D. Metivier, J. Estaquier, G. M. Fimia, L. Falasca, R. Casetti, N. Modjtahedi, J. Kanellopoulos, J. F. Mouscadet, D. M. Ojcius, M. Piacentini, M. L. Gougeon, G. Kroemer, and J. L. Perfettini. 2011. Extracellular ATP acts on P2Y2 purinergic receptors to facilitate HIV-1 infection. *The Journal of experimental medicine*. 9: 1823-34.
7. Saez, J. C., K, A. Schalper, M. A, Retamal, J. A. Orellana, K. F. Shoji, and M. V. Bennett. 2010. Cell membrane permeabilization via connexin hemichannels in living and dying cells. *Experimental cell research* 316:2377-2389.
8. MacVicar, B. A., and R. J. Thompson. 2010. Non-junction functions of pannexin-1 channels. *Trends neurosciences* 33:93-102.
9. Willecke, K., J. Eiberger, J. Degen, D, Eckardt, A. Romualdi, M. Guldenagel, U. Deutsch, and G. Sohl. 2002. Structural and functional diversity of connexin genes in the mouse and human genome. *Biol Chem* 383:725-737.
10. Schenk, U., A. M. Westendorf, E. Radaelli, A. Casati, M. Ferro, M. Fumagalli, C. Verderio, J. Buer, E. Scanziani, and F. Grassi. 2008. Purinergic control of T cell activation by ATP released through pannexin-1 hemichannels. *Sci Signal* 1:ra6.
11. Woehrle, T., L. Yip, A. Elkhal, Y. Sumi, Y. Chen, Y. Yao, P. A. Insel, and W. G. Junger. 2010. Pannexin-1 hemichannel-mediated ATP release together with P2X1 and P2X4 receptors regulate T-cell activation at the immune synapse. *Blood* 116:3475-3484.
12. Woehrle, T., L. Yip, M. Manohar, Y. Sumi, Y. Yao, Y. Chen, and W. G. Junger. 2010. Hypertonic stress regulates T cell function via pannexin-1 hemichannels and P2X receptors. *Journal of leukocyte biology* 88:1181-1189.
13. Qu, Y., S. Misaghi, K. Newton, L. L. Gilmour, S. Louie, J, E. Cupp, G. R. Dubyak, D, Hackos, and V. M. Dixit. 2011. Pannexin-1 is required for ATP release during apoptosis but not for inflammasome activation. *Journal of immunology* 186:6553-6561.
14. Chekeni, F. B., M. R. Elliott, J. K. Sandilos, S. F. Walk, J. M. Kinchen, E. R. Lazarowski, A. J. Armstrong, S. Penuela, D. W. Laird, G. S. Salvesen, B. E. Isakson, D. A. Bayliss, and K. S. Ravichandran. 2010. Pannexin 1 channels mediate 'find-me' signal release and membrane permeability during apoptosis. *Nature* 467:863-867.
15. Pelegrin, P., C. Barroso-Gutierrez, and A. Surprenant. 2008. P2X7 receptor differentially couples to distinct release pathways for IL-1beta in mouse macrophage. *Journal of immunology* 180:7147-7157.
16. Buckner, C. M., T. M. Calderon, D. W. Williams, T. J. Belbin, and J. W. Berman. 2011. Characterization of monocyte maturation/differentiation that facilitates their transmigration across the blood-brain barrier and infection by HIV: implications for NeuroAIDS. *Cellular immunology* 267:109-123,
17. Eugenin, E. A., K. Osiecki, L. Lopez, H. Goldstein, T. M. Calderon, and J. W. Berman. 2006. CCL2/monocyte chemoattractant protein-1 mediates enhanced transmigration of human immunodeficiency virus (HIV)-infected leukocytes across the blood-brain barrier: a potential mechanism of HIV-CNS invasion and NeuroAIDS. *J Neurosci* 26:1098-1106.
18. Orellana, J. A., N. Froger, P. Ezan, J. X. Jiang, M. V. Bennett, C. C. Nails, C. Giaume, and J. C. Saez. 2011. ATP and glutamate released via astroglial connexin 43 hemichannels mediate neuronal death through activation of pannexin 1 hemichannels. *Journal of neurochemistry.* 5: 826-40.
19. Orellana, J. A., D. E. Hernandez, P. Ezan, V. Velarde, M. V. Bennett, C. Giaume, and J. C. Saez. 2010. Hypoxia in high glucose followed by reoxygenation in normal glucose reduces the viability of cortical astrocytes through increased permeability of connexin 43 hemichannels. *Glia* 58:329-343.

20. Eugenin, E. A., and J. W. Berman. 2003. Chemokine-dependent mechanisms of leukocyte trafficking across a model of the blood-brain barrier. *Methods* 29:351-361.
21. Sanchez, H. A., J. A. Orellana, V. K. Verselis, and J. C. Saez. 2009. Metabolic inhibition increases activity of connexin-32 hemichannels permeable to Ca2+ in transfected HeLa cells. *American journal of physiology. Cell physiology* 297:C665-678.
22. Pelegrin, P., and A. Surprenant. 2006. Pannexin-1 mediates large pore formation and interleukin-1beta release by the ATP-gated P2X7 receptor. *The EMBO journal* 25:5071-5082.
23. Silverman, W., S. Locovei, and G. Dahl. 2008. Probenecid, a gout remedy, inhibits pannexin 1 channels. *American journal of physiology. Cell physiology* 295:C761-767.
24. Evans, W. H., E. De Vuyst, and L. Leybaert. 2006. The gap junction cellular internet: connexin hemichannels enter the signalling limelight. *The Biochemical journal* 397:1-14.
25. Siller-Jackson, A. J., S. Burra, S. Gu, X. Xia, L. F. Bonewald, E. Sprague, and J. X. Jiang. 2008. Adaptation of connexin 43-hemichannel prostaglandin release to mechanical loading. *The Journal of biological chemistry* 283:26374-26382,
26. Eugenin, E. A., S. Morgello, M. E. Klotman, A. Mosoian, P. Lento, J. W. Berman, and A. D. Schecter. 2008. Human immunodeficiency virus (HIV) infects human arterial smooth muscle cells in vivo and in vitro: implications for the pathogenesis of HIV-mediated vascular disease. *Am J Pathol* 172:1100-1111.
27. Baba, M., O. Nishimura, N. Kanzaki, M. Okamoto, H. Sawada, Y. Iizawa, M. Shiraishi, Y. Aramaki, K. Okonogi, Y. Ogawa, K. Meguro, and M. Fujino. 1999. A small-molecule, nonpeptide CCR5 antagonist with highly potent and selective anti-HIV-1 activity. *Proceedings of the National Academy of Sciences of the United States of America* 96:5698-5703.
28. Eugenin, E. A., and J. W. Berman. 2007. Gap junctions mediate human immunodeficiency virus-bystander killing in astrocytes. *J Neurosci* 27:12844-12850.
29. Eugenin, E. A., J. E. Clements, M. C. Zink, and J. W. Berman. 2011. Human immunodeficiency virus infection of human astrocytes disrupts blood-brain barrier integrity by a gap junction-dependent mechanism. *The Journal of neuroscience: the official journal of the Society for Neuroscience* 31:9456-9465.
30. Choe, H., M. Farzan, Y. Sun, N. Sullivan, B. Rollins, P. D. Ponath, L. Wu, C. R. Mackay, G. LaRosa, W. Newman, N. Gerard, C. Gerard, and J. Sodroski. 1996. The beta-chemokine receptors CCR3 and CCR5 facilitate infection by primary HIV-1 isolates. *Cell* 85:1135-1148.
31. Dragic, T., V. Litwin, G. P. Allaway, S. R. Martin, Y. Huang, K. A. Nagashima, C. Cayman, P. J. Maddon, R. A. Koup, J. P. Moore, and W. A. Paxton. 1996. HIV-1 entry into CD4+ cells is mediated by the chemokine receptor CC-CKR-5. *Nature* 381:667-673.
32. Wu, L., N. P. Gerard, R. Wyatt, H. Choe, C. Parolin, N. Ruffing, A. Borsetti, A. A. Cardoso, E. Desjardin, W. Newman, C. Gerard, and J. Sodroski. 1996. CD4-induced interaction of primary HIV-1 gp120 glycoproteins with the chemokine receptor CCR-5. *Nature* 384:179-183.
33. Wu, L., W. A. Paxton, N. Kassam, N. Ruffing, J. B. Rottman, N. Sullivan, H. Choe, J. Sodroski, W. Newman, R. A. Koup, and C. R. Mackay. 1997. CCR5 levels and expression pattern correlate with infectability by macrophage-tropic HIV-1, in vitro. *J Exp Med* 185:1681-1691.
34. Kuhmann, S. E., E. J. Platt, S. L. Kozak, and D. Kabat. 2000. Cooperation of multiple CCR5 coreceptors is required for infections by human immunodeficiency virus type 1. *J Virol* 74:7005-7015.
35. Layne, S. P., M. J. Merges, M. Dembo, J. L. Spouge, and P. L. Nara. 1990. HIV requires multiple gp120 molecules for CD4-mediated infection. *Nature* 346:277-279.
36. Gallo, S. A., C. M. Finnegan, M. Viard, Y. Raviv, A. Dimitrov, S. S. Rawat, A. Puri, S. Duren, and R. Blumenthal. 2003. The HIV Env-mediated fusion reaction. *Biochim Biophys Acta* 1614:36-50.
37. Manes, S., G. del Real, R. A. Lacalle, P. Lucas, C. Gomez-Mouton, S. Sanchez-Palomino, R. Delgado, J. Alcami, F. Mira, and A. C. Martinez. 2000. Membrane raft microdomains mediate lateral assemblies required for HIV-1 infection. *EMBO Rep* 1:190-196,
38. Carter, G. C., L. Bernstone, D. Sangani, J. W. Bee, T. Harder, and W. James. 2009. HIV entry in macrophages is dependent on intact lipid rafts. *Virology* 386:192-202.
39. Viard, M., I. Parolini, M. Sargiacomo, K. Fecchi, C. Ramoni, S. Ablan, F. W. Ruscetti, M. Wang, and R. Blumenthal. 2002. Role of cholesterol in human immunodeficiency virus type 1 envelope protein-mediated fusion with host cells. *J Virol* 76:11584-11595.
40. Iglesias, R., S. Locovei, A. Roque, A. P. Alberto, G. Dahl, D. C. Spray, and E. Scemes. 2008. P2X7 receptor-Pannexin1 complex: pharmacology and signaling. *Am J Physiol Cell Physiol* 295:C752-760.
41. Contreras, J. E., H. A. Sanchez, E. A. Eugenin, D. Speidel., M. Theis, K. Wiliecke, F. F. Bukauskas, M. V. Bennett, and J. C. Saez. 2002. Metabolic inhibition induces opening of unapposed connexin 43 gap junction hemichannels and reduces gap junctional communication in cortical astrocytes in culture. *Proc Natl Acad Set USA* 99:495-500.
42. Garre, J. M., M. A. Retamal, P. Cassina, L. Barbeito, F. F. Bukauskas, J. C. Saez, M. V. Bennett, and V. Abudara. 2010. FGF-1 induces ATP release from spinal astrocytes in culture and opens pannexin and connexin hemichannels. *Proc Natl Acad Sci USA* 107:22659-22664.
43. Khakh, B. S., and R. A. North. 2006. P2X receptors as cell-surface ATP sensors in health and disease. *Nature* 442:527-532.
44. Schenk, U., A. M. Westendorf, E. Radaelli, A. Casati, M. Ferro, M. Fumagalli, C. Verderio, J. Buer, E. Scanziani, and F. Grassi. 2008. Purinergic control of T cell activation by ATP released through pannexin-1 hemichannels. *Sci Signal* 1:ra6.
45. Schuitemaker, H., N. A. Kootstra, R. E. de Goede, F. de Wolf, F. Miedema, and M. Tersmette. 1991. Monocytotropic human immunodeficiency virus type 1 (HIV-1) variants detectable in all stages of HIV-1 infection lack T-cell line tropism and syncytium-inducing ability in primary T-cell culture. *J Virol* 65:356-363.
46. Roos, M. T., J. M. Lange, R. E. de Goede, R. A. Coutinho, P. T. Schellekens, F. Miedema, and M. Tersmette. 1992. Viral phenotype and immune response in primary human immunodeficiency virus type 1 infection. *J Infect Dis* 165:427-432.
47. Braathen, L. R., G. Ramirez, R. O. Kunze, and H. Gelderblom. 1987. Langerhans cells as primary target cells for HIV infection. *Lancet* 2:1094.
48. Orenstein, J. M., C. Fox, and S. M. Wahl. 1997. Macrophages as a source of HIV during opportunistic infections. *Science* 276:1857-1861.
49. Qi, X., Y. Koya, T. Saitoh, Y. Saitoh, S. Shimizu, K. Ohba, N. Yamamoto, and S. Yamaoka. 2007. Efficient 49. induction of HIV-1 replication in latently infected cells through contact with CD4+ T involvement of NF-kappaB activation. *Virology* 361:325-334.
50. Nicholson, J. K., G. D. Cross, C. S. Callaway, and J. S. McDougal. 1986. In vitro infection of human monocytes with human T lymphotropic virus type III/lymphadenopathy-associated virus (HTLV-III/LAV). *J Immunol* 137:323-329.
51. Swingler, S., A. M. Mann, J. Zhou, C. Swingler, and M. Stevenson. 2007. Apoptotic killing of HIV-1-infected macrophages is subverted by the viral envelope glycoprotein. *PLoS Pathog* 3:1281-1290.
52. McElrath, M. J., R. M. Steinman, and Z. A. Cohn. 1991. Latent HIV-1 infection in enriched populations of blood monocytes and T cells from seropositive patients. *J Clin Invest* 87:27-30.
53. Lambotte, O., Y. Taoufik, M. G. de Goer, C. Walton, C. Goujard, and J. F. Delfraissy. 2000. Detection of infectious HIV in circulating monocytes from patients on prolonged highly active antiretroviral therapy. *J Acquir Immune Defic Syndr* 23:114-119.
54. Williams, K. C., and W. F. Hickey. 2002. Central nervous system damage, monocytes and macrophages, and neurological disorders in AIDS. *Annu Rev Neurosci* 25:537-562,
55. Garden, G. A. 2002. Microglia in human immunodeficiency virus-associated neurodegeneration. *Glia* 40:240-251.
56. Wu, L., N. P. Gerard, R. Wyatt, H. Choe, C. Parolin, N. Ruffing, A. Borsetti, A. A. Cardoso, E. Desjardin, W. Newman, C, Gerard, and J. Sodroski. 1996. CD4-induced interaction of primary HIV-1 gp120 glycoproteins with the chemokine receptor CCR-5. *Nature* 384:179-183,
57. Choe, H., M. Farzan, Y. Sun, N. Sullivan, B. Rollins, P. D. Ponath, L. Wu, C. R. Mackay, G. LaRosa, W. Newman, N. Gerard, C. Gerard, and J. Sodroski. 1996. The beta-chemokine receptors CCR3 and CCR5 facilitate infection by primary HIV-1 isolates. *Cell* 85:1135-1148.
58. Dragic, T., V. Litwin, G. P. Allaway, S. R. Martin, Y. Huang, K. A. Nagashima, C. Cayman, P. J. Maddon, R. A. Koup, J. P. Moore, and W. A. Paxton. 1996. HIV-1 entry into CD4+ cells is mediated by the chemokine receptor CC-CKR-5. *Nature* 381:667-673.
59. Harmon, B., and L. Ratner. 2008. Induction of the Galpha(q) signaling cascade by the human immunodeficiency virus envelope is required for virus entry. *J Virol* 82:9191-9205.
60. Melar, M., D. E. Ott, and T. J. Hope. 2007. Physiological levels of virion-associated human immunodeficiency virus type 1 envelope induce coreceptor-dependent calcium flux. *J Virol* 81:1773-1785.
61. Weissman, D., R. L. Rabin, J. Arthos, A. Rubbert, M. Dybul, R. Swofford, S. Venkatesan, J. M. Farber, and A. S. Fauci. 1997. Macrophage-tropic HIV and SIV envelope proteins induce a signal through the CCR5 chemokine receptor. *Nature* 389:981-985.
62. Liu, Q. H., D. A. Williams, C. McManus, F. Baribaud, R. W. Doms, D. Schols, E. De Clercq, M. I. Kotfikoff, R. G. Collman, and B. D. Freedman. 2000. HIV-1 gp120 and chemokines activate ion channels in primary macrophages through CCR5 and CXCR4 stimulation. *Proc Natl Acad Sci USA* 97:4832-4837.
63. Erb, L., Z. Liao, C. I. Seye, and G. A. Weisman. 2006. P2 receptors: intracellular signaling. *Pflugers Arch* 452:552-562.
64. Bowler, J. W., R. J. Bailey, R. A. North, and A. Surprenant. 2003. P2X4, P2Y1 and P2Y2 receptors on rat alveolar macrophages. *Br J Pharmacol* 140:567-575.
65. Coutinho-Silva, R., D. M. Ojcius, D. C. Gorecki, P. M. Persechini, R. C. Bisaggio, A. N. Mendes, J. Marks, G. Burnstock, and P. M. Dunn. 2005. Multiple P2X and P2Y receptor subtypes in mouse J774, spleen and peritoneal macrophages. *Biochem Pharmacol* 69:641-655.
66. Ferrari, D., P. Chiozzi, S. Falzoni, M. Dal Susino, L. Melchiorri, O. R. Baricordi, and F. Di Virgilio. 1997. Extracellular ATP triggers IL-1 beta release by activating the purinergic P2Z receptor of human macrophages. *J Immunol* 159:1451-1458.
67. Kim, S. Y., J, H. Moon, H. G. Lee, S. U. Kim, and Y. B. Lee. 2007. ATP released from beta-amyloid-stimulated microglia induces reactive oxygen species production in an autocrine fashion. *Exp Mol Med* 39:820-827.
68. Solle, M., J. Labasi, D. G. Perregaux, E. Stam, N. Petrushova, B. H. Koller, R. J. Griffiths, and C. A. Gabel. 2001. Altered cytokine production in mice lacking P2X(7) receptors. *J Biol Chem* 276:125-132,
69. Save, S., and K. Persson. 2010. Extracellular ATP and P2Y receptor activation induce a proinflammatory host response in the human urinary tract. *Infect Immun* 78:3609-3615.
70. Chaves, S. P., E. C. Torres-Santos, C. Marques, V. R. Figliuolo, P. M. Persechini, R. Coutinho-Silva, and B. Rossi-Bergmann. 2009. Modulation of P2X(7) purinergic receptor in macrophages by Leishmania amazonensis and its role in parasite elimination. *Microbes Infect* 11:842-849.
71. Cavrois, M., C. De Noronha, and W. C. Greene. 2002. A sensitive and specific enzyme-based assay detecting HIV-1 virion fusion in primary T lymphocytes. *Nat Biotechnol* 20:1151-1154.
72. Murgia, M., S. Hanau, P. Pizzo, M. Rippa, and F. Di Virgilio. 1993. Oxidized ATP. An irreversible inhibitor of the macrophage purinergic P2Z receptor. *J Biol Chem* 268:8199-8203.
73. Evans, R. J., C. Lewis, G. Buell, S. Valera, R. A, North, and A. Surprenant. 1995. Pharmacological characterization of heterologously expressed ATP-gated cation channels (P2x purinoceptors). *Mol Pharmacol* 48:178-183.
74. Kadin, I., M. Ricardo-Dukelow, P. Ciborowski, and H. E. Gendelman. 2007. Cytoskeletal protein transformation in HIV-1-infected macrophage giant cells. *J Immunol* 178:6404-6415.
75. Peng, W., M. L. Cotrina, X. Han, H. Yu, L. Bekar, L. Blum, T. Takano, G. F. Tian, S. A. Goldman, and M. Nedergaard. 2009. Systemic administration of an antagonist of the ATP-sensitive receptor P2X7 improves recovery alter spinal cord injury. *Proc Natl Acad Sci USA* 106:12489-12493.
76. Lecut, C., K. Frederix, D. M. Johnson, C. Deroanne, M. Thiry, C. Faccinetto, R. Maree, R. J. Evans, P. G. Volders, V. Bours, and C. Oury. 2009. P2X1 ion channels promote neutrophil chemotaxis through Rho kinase activation. *J Immunol* 183:2801-2809.
77. Grenegard, M., K. Vretenbrant-Oberg, M. Nylander, S. Desilets, E. G. Lindstrom, A. Larsson, I. Ramstrom, S. Ramstrom, and T. L. Lindahl. 2008. The ATP-gated P2X1 receptor plays a pivotal role in activation of aspirin-treated platelets by thrombin and epinephrine. *J Biol. Chem* 283:18493-18504.

78. Malin, S. A., and D. C. Molliver. 2010. Gi- and Gq-coupled ADP (P2Y) receptors act in opposition to modulate nociceptive signaling and inflammatory pain behavior. *Mol Pain* 6:21.
79. Kalvegren, H., J. Andersson, M. Grenegard, and T. Bengtsson. 2007. Platelet activation triggered by *Chlamydia pneumoniae* is antagonized by 12-lipoxygenase inhibitors but not cyclooxygenase inhibitors. *Eur J Pharmacol* 566:20-77.
80. Pastore, S., F. Mascia, S. Gulinelli, S. Forchap, C. Dattilo, E. Adinolfi, G. Girolomoni, F. Di Virgilio, and D. Ferrari. 2007. Stimulation of purinergic receptors modulates chemokine expression in human keratinocytes. *J Invest Dermatol* 127:660-667,
81. Lemaire, I., S. Falzoni, B. Zhang, P. Pellegatti, and F. Di Virgilio. 2011. The P2X7 Receptor and Pannexin-1 Are Both Required for the Promotion of Multinucleated Macrophages by the inflammatory Cytokine GM-CSF. *J Immunol* 187:3878-3887.
82. Lees, M. P., S. J. Fuller, R. McLeod, N. R. Boulter, C. M. Miller, A. M. Zakrzewski, E. J. Mui, W. H. Witoia, J. J. Coyne, A. C. Hargrave, S. E. Jamieson, J. M. Blackwell, J. S. Wiley, and N. C. Smith. 2010. P2X7 receptor-mediated killing of an intracellular parasite, *Toxoplasma gondii*, by human and murine macrophages. *J Immunol* 184:7040-7046.
83. Darville, T., L. Welter-Stahl, C. Cruz, A. A. Sater, C. W. Andrews, Jr., and D. M. Ojcius. 2007. Effect of the purinergic receptor P2X7 on *Chlamydia* infection in cervical epithelial cells and vaginally infected mice. *J Immunol* 179:3707-3714,
84. Fairbaim, I. P., C. B. Stober, D. S. Kumararatne, and D. A. Lammas. 2001. ATP-mediated killing of intracellular mycobacteria by macrophages is a P2X(7)-dependent process inducing bacterial death by phagosome-lysosome fusion. *J Immunol* 167:3300-3307.
85. Balabanian, K., J. Harriague, C. Decrion, B. Lagane, S. Shade, F. Baleux, J. L. Virelizier, F. Arenzana-Seisdedos, and L. A. Chakrabarti. 2004. CXCR4-tropic HIV-1 envelope glycoprotein functions as a viral chemokine in unstimulated primary CD4+ T lymphocytes. *J Immunol* 173:7150-7160,
86. Woehrle, T., L. Yip, A. Elkhal, Y. Sumi, Y. Chen, Y. Yao, P. A. Inset, and W. G. Junger. 2010. Pannexin-1 hemichannel-mediated ATP release together with P2X1 and P2X4 receptors regulate T-cell activation at the immune synapse. *Blood* 116:3475-3484.
87. Wong, C. W., T. Christen, I. Roth, C. E. Chadjichristos, J. P. Derouette, B. F. Foglia, M. Chanson, D. A. Goodenough, and B. R. Kwak. 2006. Connexin37 protects against atherosclerosis by regulating monocyte adhesion. *Nat Med* 12:950-954.
88. Stout, C. E., J. L. Costantin, C. C. Naus, and A. C. Charles. 2002. Intercellular calcium signaling in astrocytes via ATP release through connexin hemichannels. *Biol Chem* 277:10482-10488.
89. Orellana, J. A., N. Froger, P. Ezan, J. X. Jiang, M. V. Bennett, C. C. Naus, C. Giaume, and J. C. Saez. 2011. ATP and glutamate released via astroglial connexin43 hemichannels mediate neuronal death through activation of pannexin 1 hemichannels. *J Neurochem*.
90. Seror, C., M. T. Melki., F. Subra, S. Q. Raza, M. Bras, H. Saidi, R. Nardacci, L. Voisin, A. Paoletti, F. Law, I. Martins, A. Amendola, A. A. Abdul-Sater, F. Ciccosanti, O. Delelis, F. Niedergang, S. Thierry, N. Said-Sadier, C. Lamaze, D. Metivier, J. Estaquier, G. M. Fimia, L Falasca, R. Casetti, N. Modjtahedi, J. Kanellopoulos, J. F. Mouscadet, D. M. Ojcius, M. Piacentini, M. L. Gougeon, G. Kroemer, and J. L. Perfettini. 2011. Extracellular ATP acts on P2Y2 purinergic receptors to facilitate HIV-1 infection. *The Journal of experimental medicine.*
91. De Vuyst, E., E. Decrock, L. Cabooter, G. R. Dubyak, C. C. Naus, W. H. Evans, and L. Leybaert. 2006. Intracellular calcium changes trigger connexin 32 hemichannel opening. *EMBO* 25:34-44.
92. Fitz, J. G. 2007. Regulation of cellular ATP release. *Trans Am Clin Climatol Assoc* 118:199-208.
93. Rettinger, J., and G. Schmalzing. 2003. Activation and desensitization of the recombinant P2X1 receptor at nanomolar ATP concentrations. *J Gen Physiol* 121:451-461.
94. Gargett, C. E., J. E. Cornish, and J. S. Wiley. 1997. ATP, a partial agonist for the P2Z receptor of human lymphocytes. *Br J Pharmacol* 122:911-917,
95. Waldo, G. L., and T. K. Harden. 2004. Agonist binding and Gq-stimulating activities of the purified human P2Y1 receptor. *Mol Pharmacol* 65:426-436.
96. Tsuda, M., Y. Shigemoto-Mogami, S. Koizumi, A. Mizokoshi, S. Kohsaka, M. W. Salter, and K. Inoue. 2003. P2X4 receptors induced in spinal microglia gate tactile allodynia after nerve injury. *Nature* 424:778-783.
97. Gao, Y., C. Xu, K. Yu, G. Li, F. Wan, S. Liu, J. Lin, H. Liu, J. Zhang, X. Li, and S. Liang. 2010. Effect of tetramethylpyrazine on DRG neuron P2X3 receptor involved in transmitting pain after burn. *Burns* 36:127-134.
98. Gunosewoyo, H., and M. Kassiou. 2010. P2X purinergic receptor ligands: recently patented compounds. *Expert Opin Ther Pat* 20:625-646.
99. Schenk, U., A. M. Westendorf, E. Radaelli, A. Casati, M. Ferro, M. Fumagalli, C. Verderio, J. Buer, E. Scanziani, and F. Grassi. 2008. Purinergic control of T cell activation by ATP released through pannexin-1 hemichannels. *Sci Signal* 1:ra6.

What is claimed is:

1. A method of treating a mammalian subject having an HIV infection, or suspected of having been exposed to HIV, comprising administering to the mammalian subject an amount of a selective P2Y$_1$ receptor inhibitor, wherein the inhibitor is MRS 2179 (2'-deoxy-N6-methyladenosine 3',5'-bisphosphate tetrasodium salt), MRS 2279 ((1R*,2S*)-4-[2-Chloro-6-(methylamino)-9H-purin-9-yl]-2-(phosphonooxy)bicyclo[3.1.0]hexane-1-methanol dihydrogen phosphate ester diammonium salt), or MRS 2500 tetraammonium salt ((1R*,2S*)-4-[2-Iodo-6-(methylamino)-9H-purin-9-yl]-2-(phosphonooxy)bicyclo[3.1.0]hexane-1-methanol dihydrogen phosphate ester tetraammonium salt).

2. The method of claim 1, wherein the mammalian subject is a human.

3. The method of claim 1, wherein the subject is further administered an additional anti-HIV therapy.

4. The method of claim 1, wherein the subject has not previously been administered a purinergic P2X$_1$, P2X$_7$, and/or P2Y$_1$ receptor inhibitor.

* * * * *

UNITED STATES PATENT AND TRADEMARK OFFICE
CERTIFICATE OF CORRECTION

PATENT NO. : 9,540,646 B2
APPLICATION NO. : 14/381727
DATED : January 10, 2017
INVENTOR(S) : Eliseo Eugenin et al.

Page 1 of 1

It is certified that error appears in the above-identified patent and that said Letters Patent is hereby corrected as shown below:

In the Specification

In Column 1, at Line 16, "This invention was made with government support under grant numbers MH070297, MH075679, MH083497, DA025567 and MH076679 awarded by the National Institute of Mental Health and grant number AI-051519 from the National Institutes of Health. The government has certain rights in the invention." should read --This invention was made with government support under grant numbers MH075679, MH070297, MH083497, DA025567, MH076679, and AI051519 awarded by the National Institutes of Health. The government has certain rights in the invention.--

Signed and Sealed this
Twelfth Day of February, 2019

Andrei Iancu
*Director of the United States Patent and Trademark Office*

SEQUENCE LISTING

<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Panx1 mimetic blocking peptide

<400> SEQUENCE: 1

Trp Arg Gln Ala Ala Phe Val Asp Ser Tyr
1               5                   10

```
<210> SEQ ID NO 2
<211> LENGTH: 10
<212> TYPE: PRT
<213> ORGANISM: Artificial Sequence
<220> FEATURE:
<223> OTHER INFORMATION: scrambled peptide

<400> SEQUENCE: 2

Phe Ala Asp Arg Tyr Trp Ala Gln Val Ser
1               5                   10

<210> SEQ ID NO 3
<211> LENGTH: 23
<212> TYPE: DNA
<213> ORGANISM: Artificial Sequence
<220> FEATURE:
<223> OTHER INFORMATION: Primer directed to human gene

<400> SEQUENCE: 3
gagaagtatg acaacagcct caa                                              23

<210> SEQ ID NO 4
<211> LENGTH: 21
<212> TYPE: DNA
<213> ORGANISM: Artificial Sequence
<220> FEATURE:
<223> OTHER INFORMATION: Primer directed to human gene

<400> SEQUENCE: 4
agtccttcca cgataccaaa g                                                21

<210> SEQ ID NO 5
<211> LENGTH: 20
<212> TYPE: DNA
<213> ORGANISM: Artificial Sequence
<220> FEATURE:
<223> OTHER INFORMATION: Primer directed to human gene

<400> SEQUENCE: 5
agaagaatgc ccgacagaga                                                  20

<210> SEQ ID NO 6
<211> LENGTH: 20
<212> TYPE: DNA
<213> ORGANISM: Artificial Sequence
<220> FEATURE:
<223> OTHER INFORMATION: Primer directed to human gene

<400> SEQUENCE: 6
ttgcaaacca gctgtgaaac                                                  20
```